United States Patent [19]

McEwen

[11] Patent Number: 4,550,726
[45] Date of Patent: Nov. 5, 1985

[54] METHOD AND APPARATUS FOR DETECTION OF BREATHING GAS INTERRUPTIONS

[76] Inventor: James A. McEwen, 8371 No. 4 Rd., Richmond, British Columbia, Canada, V6Y 2T7

[21] Appl. No.: 398,716

[22] Filed: Jul. 15, 1982

[51] Int. Cl.$^4$ ............................................ A61M 16/00
[52] U.S. Cl. ................................................ 128/202.22
[58] Field of Search ...................... 128/202.22, 204.21, 128/204.22, 204.23

[56] References Cited

U.S. PATENT DOCUMENTS

| | | | |
|---|---|---|---|
| 3,961,627 | 6/1976 | Ernst et al. | 128/202.22 |
| 4,323,064 | 4/1982 | Hoenig et al. | 128/202.22 |
| 4,326,513 | 4/1982 | Schulz et al. | 128/204.23 |
| 4,345,612 | 8/1982 | Koni et al. | 128/204.21 |

FOREIGN PATENT DOCUMENTS 0046570  3/1982  European Pat. Off. ....... 128/204.22

OTHER PUBLICATIONS

Jager; Microprocessor Based Disconnect Monitor in Surgery; UBC Engineer, pp. 28-31, Spring 1982.
Nouh; A Proposed Controlled Ventilator by Digital Computer; J. Eng. Sci., Univ. Riyadh, 6 (1), pp. 49-54 (1980).

Primary Examiner—Henry J. Recla
Attorney, Agent, or Firm—Klarquist, Sparkman, Campbell, Leigh & Whinston

[57] ABSTRACT

A method for detecting an interruption in the supply of breathing gas to a patient, and apparatus adapted to carry out the method by:

(a) during a reference time period, sensing the pressure in the patient's breathing gas;
(b) storing, in memory apparatus, reference breathing information derived from the pressure sensed during the reference time period;
(c) after the reference time period, sensing the pressure in the patient's breathing gas;
(d) comparing active breathing information derived from the pressure sensed after the reference time period with the reference breathing information; and,
(e) producing an alarm signal upon detection, during the comparing step, of predetermined variations between the reference breathing information and the active breathing information.

19 Claims, 12 Drawing Figures

METHOD AND APPARATUS FOR DETECTION OF BREATHING GAS INTERRUPTIONS

FIELD OF THE INVENTION

This application pertains to a method and apparatus for detecting an interruption in the supply of breathing gas to a patient. In the art, the terms "patient-circuit monitor", "disconnect monitor", "breathing-circuit monitor" and "low pressure alarm" are interchangeably used for such apparatus.

BACKGROUND OF THE INVENTION

"Ventilators" are medical devices for delivering a breathing gas to a patient. Typically, variables such as the patient's breathing rate or frequency, volume of breathing, and inspiratory flow rate may be controlled by the ventilator operator. Usually, ventilators employed in hospital critical care units provide a supply of air enriched with oxygen for inspiration by the patient, and may conventionally include controls for either assisting or controlling breathing, exhaled volume indicators, alarms systems, positive end expiratory pressure valves, pressure indicators, gas concentration monitors, flow indicators, and heated humidifiers for warming and humidifying the breathing gas. Ventilators intended for use with anesthetized patients are usually much simpler to operate than ventilators intended for use in critical care units, but require the anesthetist to add specific ancillary devices and accessories to the "patient breathing circuit" connecting the ventilator to the patient, as warranted by factors such as the physiological status of the patient, the nature of the surgical procedure, the anesthetic technique employed, etc.

Typically, in both anesthetic and critical care applications, the "patient breathing circuit" includes hoses which connect the ventilator and ancillary devices and accessories to an endotracheal tube inserted into the patient's trachea to permit breathing gas to pass through the trachea into the patient's lungs.

The following discussion pertains to ventilators and patient breathing circuits intended for anesthetic applications, since it is believed that these are the more demanding and crucial applications, but it should be understood that the discussion applies generally to applications in which ventilators are employed in critical care units.

It sometimes happens that the tubing used to convey breathing gas to the anesthetized patient becomes disconnected, or blocked, or develops leaks, or that the endotracheal tube becomes dislodged; any of which may result in an interruption in the supply of breathing gas to the patient. Interruption of the patient's breathing gas supply for a relatively brief period may have serious consequences including hypoxia, cardiac arrest or even death. Since an anesthetized patient is often intentionally paralyzed with curare-like drugs, and since the attending anesthetist's view of the patient may be largely obscured by the surgical drapes, the positioning of the patient, the nature of the surgical procedures, other equipment, etc., it is often not possible for the anesthetist to observe the patient and patient breathing circuit to visually detect hazardous conditions. Recent studies have shown that even very experienced anesthetists may not be able to recognize symptoms of an interruption in the patient's supply of breathing gas until after the interruption has gone undetected for a period of time sufficient to result in hypoxia, bradycardia or cardiac arrest.

"Disconnect monitors" (also known in the art as "patient-circuit monitors", "breathing-circuit monitors" or "low pressure alarms", but hereinafter collectively referred to as "disconnect monitors") are devices for monitoring a patient's breathing gas supply and for producing alarm signals upon detection of symptoms of a disconnection or blockage in the patient breathing circuit. Prior art disconnect monitors have utilized pressure sensors, gas volume sensors or gas flow sensors to monitor the pressure, volume or flow characteristics of the breathing gas supplied to a patient. Typically, such prior art disconnect monitors produce alarm signals upon detection of breathing gas pressures, volumes or flow rates which fail to meet operator defined criteria. However, such prior art disconnect monitors have proved incapable of reliably detecting certain types of disconnections or blockages in the patient breathing circuit. For example, the tubing which supplies breathing gas to the patient may become disconnected, and the open end of the tubing may be partially or totally blocked if it rests against a surgical drape, pillow or bedsheet. Such partial or total blockage of the tubing has been found to result in a back pressure within the tubing sufficient to maintain the breathing gas pressure in the vicinity of a disconnect monitor pressure sensor within acceptable limits. Accordingly, some prior art disconnect monitors have failed to produce an alarm signal even though the patient's breathing gas supply from the patient breathing circuit is completely cut off.

Some prior art disconnect monitors have also proved incapable of reliably detecting interruptions in the patient's breathing gas supply caused by partial extubation of the endotracheal tube or kinking of the breathing gas tubing, either of which may also result in back pressures sufficient to maintain the breathing gas pressure in the vicinity of the disconnect monitor pressure sensor within acceptable limits and thereby inhibit production of an alarm signal even though the patient's breathing gas supply is partially or completely cut off.

SUMMARY OF THE INVENTION

To overcome these problems, and in an effort to maximize the probability of reliably detecting an interruption in a patient's breathing gas supply, the present invention provides a method of analyzing pressure and exhalation of breathing gas by the patient to develop a reference breathing waveform representative of "normal" pressure fluctuations in the patient breathing circuit over a representative "normal" inhalation and exhalation breathing cycle of the patient during a reference time period initiated by an operator. The reference time period ends after a reference breathing waveform has been developed. The pressure in the patient's active or ongoing inhalation and exhalation breathing cycles is then monitored to develop active breathing waveforms representative of pressure fluctuations in each active breathing cycle. Each active breting waveform is compared to the reference breathing waveform and an alarm signal is produced upon detection of any one of a wide range of predetermined variations between the reference breathing waveform and the active breathing waveform. Apparatus adapted to carry out the foregoing method is provided. The apparatus incorporates an optional gas sensor capable of reliably deriving gas pressure information from an oxygen analyzer. The derived gas pressure information may be compared with gas pressure information derived from a conventional gas pressure sensor so as to crosscheck the gas pressure information and detect a malfunction of either the optional gas sensor or the conventional gas pressure sensor, or their associated signal processing circuitry.

The invention is believed to be capable of more reliably detecting interruptions in a patient's breathing gas supply than are prior art disconnect monitors because, unlike prior art disconnect monitors which, for example, simply monitor pressure in the breathing circuit to ensure that the pressure cycles above an operator defined lower limit, the present invention monitors a broad range of parameters which characterize the breathing cycle waveform.

The invention provides a method for detecting an interruption in the supply of breathing gas to a patient, comprising the steps of:
  (a) during a reference time period indiated by a operator, sensing the pressure in the patient's breathing gas;
  (b) storing, in memory apparatus, reference breathing information derived from the pressure sensed during the reference time period in respect of a normal breathing cycle of the patient;
  (c) after the reference time period, sensing the pressure in the patient's breathing gas;
  (d) comparing active breathing information derived from the pressure sensed after the reference time period in respect of an active breathing cycle of the patient with the reference breathing information; and,
  (e) producing an alarm signal upon detection, during the comparing step, of predetermined variations between the reference breathing information and the active breathing information.

Preferably, before the storing step, a referential comparison is made between:
  (a) breathing information derived from the pressure in the patient's breathing gas during a first referential breathing cycle of the patient; and,
  (b) breathing information derived from the pressure in the patient's breathing gas during a second referential breathing cycle of the patient which follows the first referential breathing cycle;
and the storing step is taken only if the breathing information derived from the pressure sensed during said first referential breathing cycle differs, by no more than a selected amount, from the breathing information derived from the pressure sensed during the second referential breathing cycle; otherwise, the referential comparing step is repeated.

The breathing information may include such parameters as the average breathing gas pressure sensed during the breathing cycle in respect of which the breathing information is derived; the maximum breathing gas pressure sensed during the breathing cycle in respect of which the breathing information is derived; the minimum breathing gas pressure sensed during the breathing cycle in respect of which the breathing information is derived; ratio of the time, during the breathing cycle in respect of which the breathing information is derived, the patient inspires breathing gas, to the time, during the breathing cycle in respect of which the breathing information is derived, the patient expires breathing gas; the period of the breathing cycle in respect of which the breathing information is derived.

The alarm signal is produced upon detection of any of the following conditions:

(a) detection of an active breathing cycle having a breathing gas pressure in excess of about 45 cmH$_2$O;
  (b) detection of an active breathing cycle having a breathing gas pressure less than about −8 cmH$_2$O;
  (c) detection, for at least 15 seconds during an active breathing cycle, of breathing gas pressures less than the greater of:
    (i) 5 cmH$_2$O; and,
    (ii) the average breathing gas pressure of said representative normal breathing cycle;
  (d) detection of an active breathing cycle having a period longer than about 30 seconds;
  (e) detection, during the reference time period, of ten successive referential breathing cycles, each having an average pressure which differs, by more than about ten percent, from the average pressure of the immediately following referential breathing cycle;
  (f) detection of an active breathing cycle having a maximum breathing gas pressure which differs, by more than about 13 percent, from the maximum breathing gas pressure of the representative normal breathing cycle;
  (g) detection of an active breathing cycle having a minimum breathing gas pressure which differs, by more than about 17 percent, from the minimum breathing gas pressure of the representative normal breathing cycle;
  (h) detection of an active breathing cycle having a period which differs, by more than about 17 percent, from the period of the representative normal breathing cycle;
  (i) detection of an active breathing cycle having an average breathing gas pressure which differs, by more than about 17 percent, from the average breathing gas pressure of the representative normal breathing cycle;
  (j) detection of an active breathing cycle during which the ratio of the time the patient inspires breathing gas, to the time the patient expires breathing gas, is less than about 0.2 or more than about 4.0;
  (k) detection of an active breathing cycle duirng which the ratio of the time the patient inspires breathing gas to the time the patient expires breathing gas differs, by more than about 25 percent, from the ratio of time the patient inspires breathing gas during the representative normal breathing cycle to the time the patient expires breathing gas during the representative normal breathing cycle.

The invention also provides apparatus for detecting an interruption in the supply of breathing gas to a patient, comprising pressure sensing means for sensing the pressure in the patient's breathing gas and for producing an output signal representative thereof; memory apparatus for storing reference breathing information derived from the output signal during a reference time period initiated by an operation; signal comparison means for comparing:
  (a) active breathing information derived from the output signal after the reference time period; with
  (b) the reference breathing information; and, alarm means for producing an alarm signal upon detection, by the comparison means, of a predetermined variation between the active breathing information and the reference breathing information.

DESCRIPTION OF THE PREFERRED EMBODIMENT

I. Background

Figure 1:
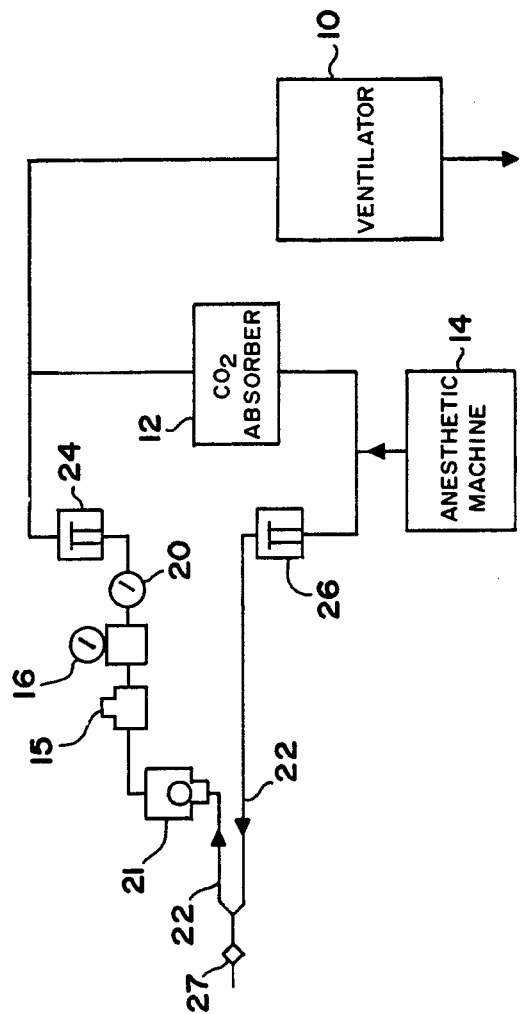
FIG. 1 is a block diagram showing the configuration of a typical patient breathing circuit.

FIG. 1 is a block diagram showing the configuration of a typical patient breathing circuit including a gas-powered ventilator 10 for dependably delivering a desired volume of gas to a patient at a specified rate, a carbon dioxide absorber 12 for removing carbon dioxide from that portion of gas exhaled by the patient which may be intentionally directed back to the patient for inhalation with fresh gas, anesthetic machine 14 for supplying a desired mixture of fresh gases in sufficient quantity, a gas monitor 15 for providing an indication of the concentration of a specific gas, a spirometer 16 for providing an indication of the volume of gas passing through a portion of the patient breathing circuit, a pressure guage 20 for providing an indication of the instantaneous gas pressure, and positive end expiratory pressure ("PEEP") valve 21 for preventing a return to zero pressure at the end of exhalation.

Hoses 22 facilitate the flow of breathing gas to and from endotracheal tube connector 27, and throughout the patient breathing circuit. One-way valves 24 and 26 facilitate the flow of gas in the desired direction in the patient breathing circuit Although FIG. 1 shows one typical patient breathing circuit, a wide variety of other configurations may be employed for specific applications: for example, a coaxial or "Bain" patient breathing circuit which does not require valves 24 and 26 and carbon dioxide absorber 12 is widely used.

In operation, a patient breathing circuit such as the one shown in FIG. 1 is typically assembled for a specific patient and for a specific surgical procedure by an anesthetist. The controls on anesthetic machine 14 are set to supply a desired mixture of gases, typically nitrous oxide, oxygen and in some cases a volatile anesthetic agent, at a sufficient rate of flow. The controls on ventilator 10 are set to supply the patient, via the patient breathing circuit, endotracheal tube connector 27 and endotracheal tube (not shown in FIG. 1) with gas at a specified "minute volume", i.e. at a specified number of breathing cycles or artificial breaths per minute and at a specified volume per cycle. Ventilator 10 begins to supply the specified volume to the patient breathing circuit at the beginning of a breathing cycle (typically by compressing a bellows within the ventilator). An equivalent volume of gas, consisting of fresh gas supplied by anesthetic machine 14 together with some gas from ventilator 10 which has passed through carbon dioxide absorber 12, passes through one way valve 26 and hose 22 to the patient through endotracheal tube connector 27. When ventilator patient breathing circuit and has returned to its normal 10 has pushed the specified volume of gas into the patient breathing circuit and has returned to its normal state during the expiratory phase of the breathing cycle, expired gas from the patient passes through endotracheal tube connector 27, hose 22, PEEP valve 21, gas mobitor 15, spirometer 16, pressure gauge 20 and one-way valve 24. Some of the expired gas remains in ventilator 10 until the next breathing cycle, some is drawn off through ventilator 10 to a scavenging system (not shown) which safely removes it from the operating room, and some passes into carbon dioxide absorber 12. The above described cycle is then repeated at the set rate.

The graphs of FIG. 2 were obtained by measuring pressure (in cmH2O) at the inlet port of carbon dioxide absorber 12 of a patient breathing circuit configured according to FIG. 1.

Figure 2A:
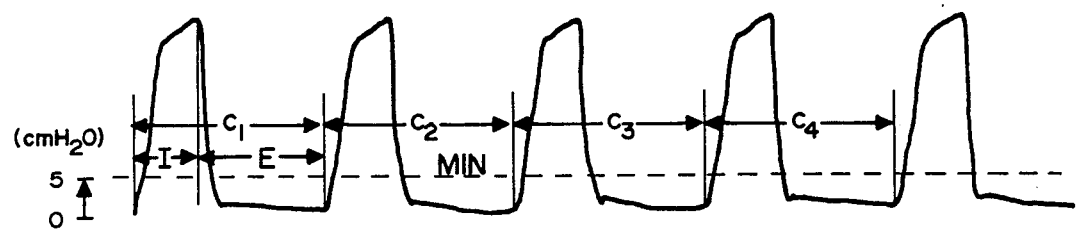
FIGS. 2A through 2E are graphs in which patient breathing circuit pressure in cmH2O is plotted as the ordinate versus time as the abscissa.

FIG. 2A shows a normal patient breathing circuit pressure waveform comprising a series of "breathing cycles" $C_1$, $C_2$, $C_3$, etc., each breathing cycle comprising an inspiratory phase "I" and an expiratory phase "E" as shown in FIG. 2A with reference to breathing cycle $C_1$.

Prior art disconnect monitors typically enable the operator to define an expected minimum peak breathing circuit pressure. The minimum peak breathing circuit pressure is usually defined to be some pressure less than the peak pressure which the operator expects will be generated in the patient breathing circuit, e.g. some pressure between 2–15 cmH2O. For example, with reference to FIG. 2A, the minimum peak breathing pressure might be defined by the operator to coincide with the broken line marked "min" which represents a peak pressure of 5 cmH2O. In operation, such typical prior art disconnect monitors monitor the pressure in the patient breathing circuit which normally continually cycles by rising above, and then falling below, the defined minimum peak breathing circuit pressure at a frequency defined by the ventilatory rate. Normally, between four and thirty breathing cycles per minute are completed, depending on the patient's age, physiologic status, etc., and the anethetic technique. Prior art disconnect monitors of this sort produce alarm signals if the pressure in the patient breathing circuit fails to rise above the operator-defined minimum peak breathing circuit pressure within a specified period of time. Typically, this period of time in some prior art disconnect monitors is fixed at about 15 seconds, and in other prior art disconnect monitors can be set by the operator, e.g. to some time between 27–30 seconds.

Figure 2B:
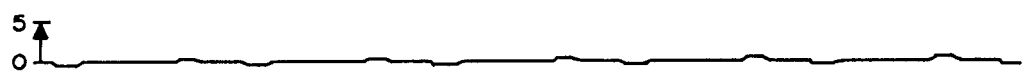

FIG. 2B shows a patient breathing circuit pressure waveform obtained by completely disconnecting the breathing gas tubing from the endotracheal tube (which would completely cut off the patient's breathing gas supplied from the patient breathing circuit), and leaving the end of the gas tubing free of obstructions. As FIG. 2B shows, the patient breathing circuit pressure remains approximately constant at 0 cmH$_2$O under these conditions. Prior art disconnect monitors which operate by detecting continued cycling of the breathing gas pressure above an operator defined minimum peak pressure can usually reliably detect a failure of the sort shown in FIG. 2B.

Figure 2C:

FIG. 2C shows a patient breathing circuit pressure waveform obtained under conditions similar to those used to produce FIG. 2B, but in which the end of the breathing gas tubing was completely obstructed. In practice such a condition might occur due to partial extubation of the endotracheal tube, or due to disconnection of the endotracheal tube connector accompanied by kinking of a breathing hose or complete occlusion of the aperture of the breathing hose by a drape, pillow, sheet, or similar materials. Some prior art disconnect monitors of the sort described above have proved incapable of reliably detecting a failure of the sort shown in FIG. 2C because the patient breathing circuit pressure continues to cycle above the minimum peak breathing circuit pressure typically defined by the operator, due to the backpressure caused by the obstructed tubing, despite the fact that the patient's breathing gas supply from the patient breathing ciruit is completely cut off.

Figure 2D:

FIG. 2D shows a patient breathing circuit pressure waveform obtained under conditions similar to those used to produce FIG. 2B, but in which the end of the disconnected breathing gas tubing was about 50% obstructed with a surgical drape. A study of disconnections in patient breathing circuits has revealed that a majority of such disconnections have occurred at the endotracheal tube connector. When this happens, it is quite possible for the breathing gas tubing to fall against, and become partially obstructed by a surgical drape, pillow or bedsheet as contemplated by FIG. 2D. A prior art disconnect monitor capable of having an operator defined minimum peak breathing circuit pressure of about 2 cmH$_2$O or less could fail to reliably detect the condition depicted in FIG. 2D.

Figure 2E:
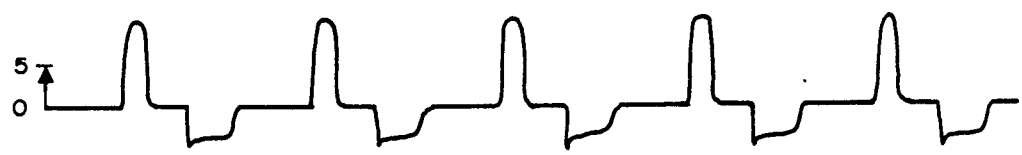

FIG. 2E shows a patient breathing circuit pressure waveform obtained under conditions similar to those used to produce FIG. 2B, but in which the end of the disconnected breathing gas tubing was about 75% obstructed with a surgical drape. FIG. 2E is considered to be representative of a patient breathing circuit pressure waveform for an incident which ultimately resulted in a patient's death. A prior art type disconnect monitor of the type described above which was employed during this incident failed to produce an alarm signal, despite the complete cutoff of the patient's breathing gas supply from the patient breathing circuit. The monitor in question was examined immediately after the incident and was found to be functioning according to the manufacturer's specifications. An examination of FIG. 2E suggests that the failure likely occurred because the patient breathing circuit pressure continued to cycle above the minimum peak breathing circuit pressure defined by the operator due to the backpressure caused by the partially obstructed tubing, despite the fact that the patient's breathing gas supply was completely cut off.

II. Introduction to the Preferred Embodiment:

The present invention represents an attempt to overcome some obvious deficiencies of prior art disconnect monitors, including a failure to trigger an alarm despite a complete cutoff of the patient's breathing gas supply from the patient breathing circuit. Other deficiencies of prior art disconnect monitors revealed by the inventor's investigations include either a complete inability to detect, or an inability to consistently and reliably detect, failures such as: disconnections in the patient breathing circuit other than at the endotracheal tube connector, associated with entrainment of air into the patient breathing circuit; disconnections associated with the use of positive end expiratory pressure ("PEEP") valves; kinks in the breathing circuit tubing leading to hazardously high pressures at the endotracheal tube; partial extubation (i.e. partial dislodging) of the endotracheal tube such that the aperture of the tube is located, and is partially occluded, inside the patient's mouth; and complete extubation with the endotracheal tube connected to a coaxial breathing hose having high flow resistance. The present invention attempts to maximize the probability of reliably detecting any of the above noted failures or interruptions in the patient breathing gas supply.

In operation, a reference time period is initiated by an operator. After the initiation of the referenced time period, apparatus of the preferred embodiment begins by sampling the pressure in the patient breathing circuit every one-tenth of a second, and averaging the sampled pressure values over a period of about ten seconds. The average value of the pressure so determined is then used to detect the beginning of the next breathing cycle, which is defined as the "first referential breathing cycle", labeled C$_1$, in FIG. 2A. The average pressure, maximum pressure, minimum pressure, inspiration time to expiration time ratio (hereinafter called the I/E ratio), and total period of the first referential breathing cycle C$_1$, are determined by sampling the breathing circuit pressure every one-tenth of a second during first referential breathing cycle C$_1$. The values of average pressure, maximum pressure, minimum pressure, I/E ratio and total period so determined are then compared to like values determined in similar fashion by sampling the breathing circuit pressure during a second referential breathing cycle C$_2$, which immediately follows first referential breathing cycle C$_1$. If all values determined in respect of second referential breathing cycle C$_2$ are within about ten percent of corresponding values determined in respect of first referential breathing cycle C$_1$, the two breathing cycles are deemed to be sufficiently similar, and the values from both cycles are averaged together, thereby defining a "reference breathing cycle" which is deemed to represent the patient's "normal" breathing condition. The averaged reference breathing cycle information is stored in a memory device for later use as hereinafter described. If the values determined in respect of referential breathing cycle C$_2$ are not sufficiently similar to the corresponding values determined in respect of referential breathing cycle C$_1$, a third referential breathing cycle C$_3$ which immediately follows second referential breathing cycle C$_2$ is sampled and the values so determined are compared to those determined in respect of second referential breathing cycle C$_2$. This process is repeated until two sufficiently similar consecutive referential breathing cycles are found so that a "reference breathing cycle" can be defined.

After the reference breathing cycle is defined, the apparatus continues to sample the pressure in the patient breathing circuit every one-tenth of a second during each "active" or ongoing breathing cycle of the patient. At the end of each active breathing cycle, the values of average pressure, maximum pressure, minimum pressure, I/E ratio, and total period for that active breathing cycle are determined and compared to the corresponding values previously derived in respect of the reference breathing cycle. If all of the active breathing cycle values are sufficiently similar (as hereinafter explained under the heading "Alarms") to the corresponding values previously derived in respect of the reference breathing cycle, and provided certain other criteria are met (also hereinafter explained under the heading "Alarms") the active breathing cycle is deemed to be sufficiently similar to the reference breathing cycle; and therefore sufficiently similar to the patient's normal breathing condition that there should be no cause for alarm. Otherwise, audible and visual alarms are triggered to alert the operating room personnel to a problem which may require their attention.

Because the patient's physiological status may change during a surgical procedure, and because settings of specific parameters of the anesthetic ventilator and other related devices connected to the patient's breathing circuit may deliberately be changed during the surgical procedure, in a manner such that the patient's breathing pattern may also change, the operator may wish to redefine the reference breathing cycle by sampling and averaging successive similar breathing cycles as described above. This reduces the probability of continuing false alarms that might otherwise be triggered.

In the preferred embodiment, an optional electronic signal proportional to pressure in the patient breathing circuit is obtained by modifying (as hereinafter described) the output of a conventional gas monitor such as an oxygen analyzer which is normally included in the patient breathing circuit, so that signals proportional to both the concentration of the gas and to changes in the partial pressure of the gas can be derived, sampled and analyzed. These signals are analyzed to check the function and calibration of the primary pressure sensing means at start-up, during referential breathing cycles, and during active breathing cycles. Additionally, the output signal from the primary pressure sensing means may be used to check the function and calibration of the gas monitor at start-up, during referential breathing cycles and during active breathing cycles as hereinafter described.

Figure 3:
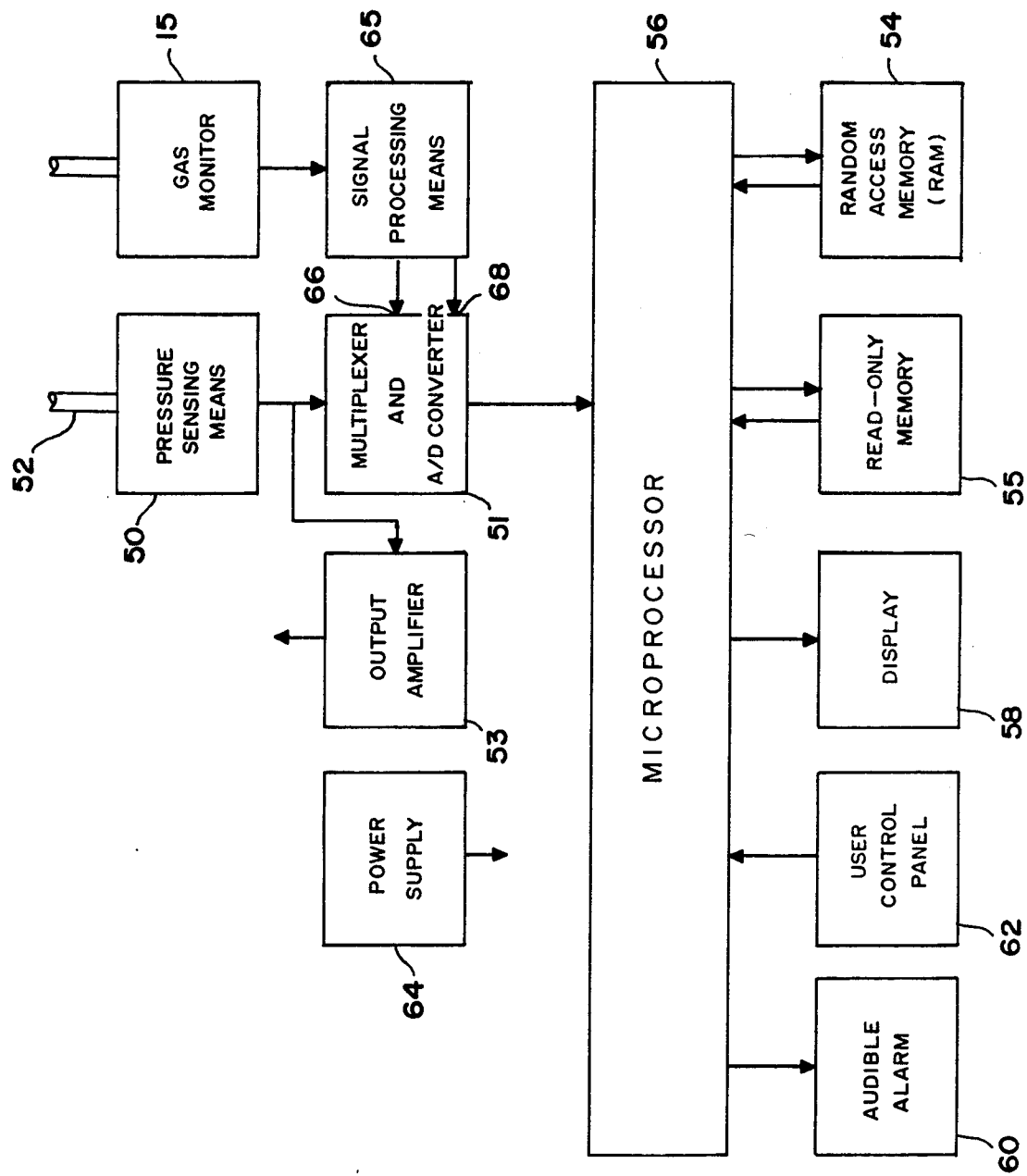
FIG. 3 is a block diagram of an apparatus for detecting an interuption in the supply of breathing gas to a patient, according to the preferred embodiment.

FIG. 3 is a block diagram which illustrates the operation of the preferred embodiment of the present invention. A pressure sensing means 50 such as an electronic pressure transducer is coupled via hose 52 into the patient breathing circuit, preferably at endotracheal tube connector 27. If connection at endotracheal tube connector 27 is inconvenient, then hose 52 may be connected into the patient breathing circuit near the inspiratory valve of carbon dioxide absorber 12, or near the oxygen analyzer (if used), or at another convenient position in the particular configuration of breathing circuit employed, preferably close to endotracheal tube connector 27. Pressure sensing means 50 senses the breathing gas pressure in the patient breathing circuit and produces an output signal representative of that pressure. This output signal is digitized by combined multiplexer and analog to digital converter 51. The same output signal is also amplified by output amplifier 53 so that it may be connected to a recording or display means (not shown).

Memory apparatus such as random access memory 54 is provided for storing the reference breathing information. Memory apparatus such as read-only memory 55 is provided for storing the computer program which controls the operation of microprocessor 56. A signal comparison means including microprocessor 56 is provided for comparing each active breathing cycle with the reference breathing information stored in memory apparatus 54. An alarm means, such as display 58 (preferably an alpha-numeric display) is provided for producing an alarm signal, such as a visible message, upon detection, by microprocessor 56, of any of the alarm conditions discussed hereinafter under the heading "Alarms". The alarm means may also include an audible alarm 60 for producing an audible alarm signal.

A user control panel 62 is provided to enable temporary suppression of the audible alarm, and to enable the operator initiate a reference time period in order to first define the reference breathing information, or to redefine the reference breathing information by causing microprocessor 56 to replace the information stored in memory apparatus 54 with information defining a new reference breathing cycle distinct from any previously defined reference breathing cycle.

As mentioned above, an optional electronic signal proportional to changes in the pressure in the patient breathing circuit may be derived by modifying the circuitry of a sensing means such as conventional gas monitor 15 so that a first output signal representative of a time-varying component of the breathing gas partial pressure is obtained, to be filtered and amplified by signal processing means 65, and separated by signal processing means 65 into a second output signal representative of a time-varying component of the breathing gas partial pressure, which time-invariant component varies in proportion to the gas concentration. The first and second output signals are connected, via external signal ports 66 and 68, to multiplexer and analog to digital converter 51. Digital samples of these signals are employed as hereinafter described to check the function and calibration of pressure sensing means 50, and to detect alarm conditions associated with referential and active breathing cycles. In a similar manner, a third output signal produced by pressure sensing means 50 may be used to check the function and calibration of gas monitor 15 and signal processing means 65.

The apparatus of the preferred embodiment is powered by a rechargeable battery operated power supply 64, except for signal processing means 65 which is incorporated into, and powered by, the power supply of gas monitor 15.

The preferred embodiment will first be described from the point of view of a typical user such as an operating room nurse or technician. A technical description of the construction and operation of the preferred embodiment will then be provided, followed by a dicussion of the software programming for the microprocessor used in the preferred embodiment.

III. Operation by Typical User

(a) Self-Test Mode of Operation

Figure 4:
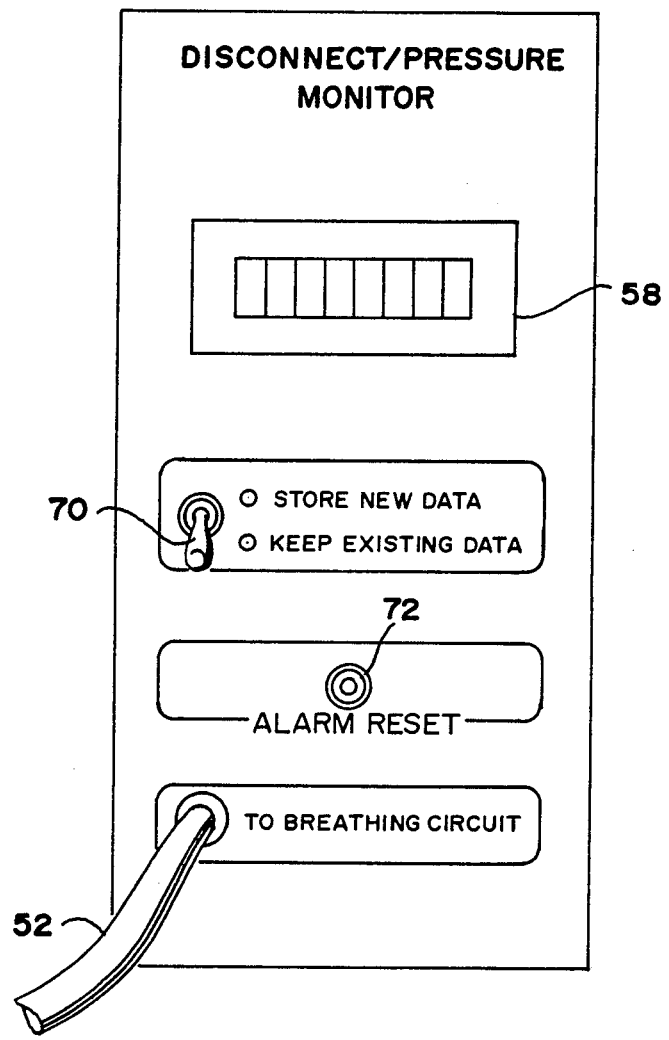
FIG. 4 is a pictorial representation of a control/display panel for the apparatus of FIG. 1.

FIG. 4 shows a control/display panel for the apparatus of the preferred embodiment. The apparatus is activated by moving an "on/off" switch (not shown in FIG. 4) from the "off" position to the "on" position, although an automatic pressure sensitive switch connected to anesthesia ventilator 10 could be employed instead of an on/off switch. The apparatus automatically enters a "self-test" mode of operation which is indicated by scrolling the message "*0*0*0*0*0*" across display 58, so that the operator can verify that all the segments of alpha-numeric display 58 are functioning. Audible alarm 60 is also activated so that the operator can verify that it is working.

During the "self-test" mode of operation, the apparatus samples the signals present at external signal ports 66 and 68 of signal processor 65 (FIG. 3) and analyzes those signals to determine whether or not a suitably modified gas analyzer has been incorporated into the patient breathing circuit. After two seconds the apparatus terminates the "self-test" mode, silences audible alarm 60, displays the message text "READY" on display 58 and enters the "normal" mode of operation. If the apparatus determines that a suitably modified gas analyzer has not been incorporated in the patient breathing circuit, then the message text "NO 02 ANALYSER" is displayed on display 58 for two seconds. The apparatus then enters the "wait" sub-mode of the "normal" operation.

(b) Normal Mode of Operation:

The normal mode of operation is divided into four sub-modes: a "wait" mode during which the apparatus waits for the operator to activate the learning mode; and therby initiate a reference time period a "learning" mode during which the reference breathing information is defined and stored; an "active" mode during which the patient's active breathing pressure cycles are sampled and compared with the stored reference breathing information; and a "calibrate" mode which allows the operator to verify the accuracy of pressure sensing means 50, test the condition of battery operated power supply 64, and test the condition of the signals at ports 66 and 68.

The "learning" mode is manually activated by depressing switch 70 after "normal" breathing conditions have been established in the patient breathing circuit. This action initiates a reference time period. Once the reference breathing information has been successfully defined, or "learned", the apparatus automatically ends the reference time period, exits the "learning" mode and enters the "active" mode.

If the apparatus has previously determined that a suitably modified gas monitor has been incorporated into the patient breathing circuit, then, during the "learning mode of operation the apparatus also averages the signal proportional to changes in pressure that is transmitted from gas analyzer 15 via external port 68, over the same ten-second interval during which the apparatus averages the signal from pressure sensing means 50 as described previously. Samples are taken at one-tenth second intervals. When averaging is complete, a reference breathing cycle based on the signal proportional to the pressure in the patient breathing circuit as detected by the modified gas analyzer, is established in a manner exactly similar to that used to derive the reference breathing cycle from the signals produced by pressure sensing means 50.

When both reference breathing cycles have been established, the apparatus performs a "cross check" of pressure sensing means 50 and gas analyzer 15. If the difference between the maximum pressure and minimum pressure which in part defined the reference cycle detected by pressure sensing means 50 is sufficiently similar to the difference between the maximum and minimum pressure which in part defines the reference cycle as detected by gas analyzer 15, after adjustments to compensate for the different methods of detection, then the apparatus proceeds into the "active" mode.

However, if the quantities described differ by more than about ten percent, it is assumed that either pressure sensing means 50 or modified gas analyzer 15 with signal processing means 65 is not operating properly, and the message "CHECK SENSORS" is displayed on display 58.

In the "active" mode, the pressure in the patient breathing circuit is sensed every one-tenth of a second and, at the end of each active breathing cycle, the sampled pressure values are used to define the characteristics of the active breathing cycle. The active breathing cycle information is compared against certain absolute criteria (hereinafter described under the heading "Alarms") and against certain relative criteria (also hereinafter described under the heading "Alarms"). Audible alarm 60 is sounded and text messages are displayed on display 58 if any of the absolute or relative criteria are not met. Otherwise, display 58 displays either the symbol "$\wedge$" indicating the inspiratory phase of an active breathing cycle, or the symbol "—" indicating the expiratory phase of an active breathing cycle.

Also in the active mode, the values of maximum pressure, minimum pressure, average pressure, I/E ratio and period of the active breathing cycle waveform as detected by modified gas analyzer 15 are compared to similar values defining the reference breathing cycle as previously determined by the modified gas analyzer, and provided certain criteria are met (as hereinafter explained under the heading "Alarms") the active breathing cycle is deemed to be suffieiently similar to the patient's "normal" breathing condition that there should be no cause for alarm. In addition, the value of the signal sensed at external signal input 66 is sampled, and provided certain criteria are met (also described under the heading "Alarms") the concentration of the selected gas in the patient breathing circuit is deemed to be acceptable and hence no cause for alarm. Otherwise, audible and visual alarms are triggered to alert the operating room personnel to a problem which may require their attention.

Switch 70 may be used during the "active" mode, to cause microprocessor 56 to replace or update the stored reference breathing cycle information with information defining a new reference breathing condition, provided that alarm conditions has been detected. Switch 70 thus enables the operator to adapt the apparatus to changes in the settings of the ventilator and other related devices, and to changes in the patient's physiological status (which may involve changes in the patient's breathing condition), but will not allow the apparatus to "learn" new reference breathing information in the presence of an alarm condition.

Alarm suppression means comprising switch 72 is provided for temporarily suppressing the audible alarm signal produced by audible alarm 60. If switch 72 is depressed, the audible alarm is suppressed for 30 seconds only, to ensure that alarms are not ignored. The audible alarm is permanently suppressed only when the condition which triggered production of the alarm has been corrected.

Switches 70 and switch 72 together enable the operator to force microprocessor 56 to replace or update reference breathing cycle information even in the presence of alarm conditions, as may be required, for example, if a change in the patient's physiological status has resulted in a change in the patient's breathing condition, which may in turn cause an alarm condition. To cause microprocessor 56 to "learn" new breathing cycle information in the presence of an alarm condition, the operator must activate switch 72 and keep it activated while momentarily activating switch 70 twice. This requirement for deliberate and simultaneous activation of two switches is intended to prevent accidental "learning" during abnormal or alarm conditions, while also permitting "learning" following an anticipated change in patient or equipment.

Switch 70 and switch 72 additionally enable the operator to enter the "calibration" mode. To enter the calibration mode, the operator must activate switch 72 and keep it activated while activating switch 70 three times.

The "calibration" mode of operation is divided into four sub-modes: pressure calibration, battery level testing, "auxiliary signal 1 testing" and "auxiliary signal 2 testing". When the calibration mode is entered, the apparatus assumes the "pressure calibration" mode of operation. In this mode, the pressure in the patient breathing circuit is sampled every one-tenth of a second, and the resulting value is displayed on display 58. This allows the operator to verify the calibration of pressure sensing means 50 with respect to a known standard.

If the apparatus is in the pressure calibration mode, then the "battery level testing" mode of operation may be entered by momentarily activating switch 70. The apparatus then samples the battery voltage every one-tenth of a second, and displays the resulting value on display 58.

If the apparatus is in the battery level testing mode, then the "auxiliary signal 1 testing" and "auxiliary signal 2 testing" modes may be entered by momentarily activating switch 70 once or twice. The auxiliary signal testing modes allow the operator to test the condition of signals at external inputs 66 and 68 by sampling the appropriate signal every one-tenth second and displaying the result on display 58.

Activation of switch 70 a fourth time causes the apparatus to revert to the "pressure calibration" sub-mode.

The "calibration" mode of operation is terminated when the operator activates switch 72 and keeps it activated while activating switch 70 three times.

IV. Alarms

Any one of the conditions hereinafter described may result in production of an audible alarm signal by audible alarm 60 and in the display, on display 58, of a message text defining the condition which triggered the alarm signal. In the preferred embodiment, display 58 is an eight-character alpha-numeric display comprising two Litronix DL 1416 intelligent alpha-numeric displays. Messages comprised of fewer than nine characters are displayed "as is" on display 58. Longer messages are scrolled across display 58 twice in rotating "billboard" fashion. Audible alarm 60 is preferably a SONALERT TM audible alarm.

The message text "MALFUNCTION" is displayed on display 58 upon detection (by the software) of an inability of the apparatus to complete any of its programmed tasks in a given period of time. Such an event would be indicative of a major failure within the apparatus.

The message text "DEAD BATTERY DPM OFF" is displayed on display 58 if the voltage of battery 64 falls below 9.6 volts, which is considered too low to power the apparatus for dependably monitoring pressure in the patient breathing circuit.

The message text "LOW BATTERY" is displayed on display 58 once every 12.8 seconds upon the detection, at any time, of a voltage at battery 64 less than 10.6 volts. This serves as a warning to the operator of a potential failure of battery 64.

The message text "HIGH PRESSURE" is displayed on display 58 upon detection, during any active breathing cycle, of a breathing gas pressure in excess of about 45 $cmH_2O$. The message text "NEGATIVE PRESSURE" is displayed on display 58 upon detection, during any active breathing cycle, of a breathing gas pressure lower than about $-8$ $cmH_2O$. These limits represent the maximum and minimum breathing gas pressures which may occur in a patient breathing circuit without endangering the patient.

The message text "LOW PRESSURE FOR 15 SEC" is displayed on display 58 upon detection, for at least 15 seconds, of breathing circuit pressures which are less than the greater of either 5 $cmH_2O$, or, the average breathing gas pressure of the representative normal reference breathing cycle. This condition could occur, for example, if part of the patient circuit had become disconnected, or if the patient's breathing gas supply was interrupted for some reason.

The message text "PERIOD>30 SEC" is displayed on display 58 upon detection of any active breathing cycle which lasts longer than 30 seconds. A 30-second breathing cycle is considered to be the longest breathing cycle that would normally be encountered in a patient breathing circuit, and may be indicative of a change in the patient's physiologic status, or of an interruption or blockage in the patient's breathing gas supply, either of which may require attention.

The message texts "I/E>4.0" or "I/E<0.2" are displayed, respectively on display 58 upon detection of any active breathing cycle during which the ratio of the time the patient inspires breathing gas to the time the patient expires breathing gas is greater than about 4.0 or less than about 0.2. These conditions represent the range of values for the ratio of inspiration time to expiration time normally found in patient breathing circuits. Inspiration time to expiration time ratios outside these limits may indicate conditions requiring attention.

In the presence of external signals such as those from modified gas analyzer 15, which in the preferred embodiment is a Critikon Oxychek TM oxygen analyzer modified as hereinafter described, the message text "CHECK 02 SENSOR" is displayed on display 58 upon the detection, at any time, of an oxygen concentration less than about 21 percent. This could indicate either a malfunction of the gas analyzer or a low level of oxygen in the patient breathing circuit, either of which would require attention.

The message text "INCONSISTENT CYCLES" is displayed on display 58 upon detection, during the learning mode, of ten successive referential breathing cycles in which the values of the parameters defining a given breathing cycle differ by more than about ten percent from the values of the parameters defining the referential breathing cycle immediately preceding the given cycle. This may be indicative of conditions such as an erratic patient breathing cycle, or an intermittent blockage or interruption of the patient's breathing gas supply, either of which would require attention.

During the "learning" mode, the message text "CHECK SENSORS" is displayed on display 58 upon detection of external signals at ports 66 and 68 if the "peak to peak" output of pressure sensing means 50 differs, by more than about 15 percent, from the peak to peak pressure detected by modified gas analyzer 15 during a given breathing cycle after adjustments to compensate for the different methods of pressure detection. This may be indicative of a miscalibration or malfunction of either pressure sensing means 50 or gas analyzer 15 and signal processing means 65, either of which may require attention.

The message text "CHECK 02 SENSOR" is displayed on display 58 if the output signals from a modified gas analyzer are connected to ports 66 and 68, and if there is a change of more than about ten percent in the concentration of oxygen in the patient breathing circuit at the beginning and end of a breathing cycle. This could be a result of conditions such as a malfunction of gas analyzer 15, or a change in the concentration of oxygen in the patient breathing circuit, either of which may require attention.

Additional alarms are produced if any of the values of average pressure, maximum pressure, minimum pressure, I/E ratio, or total period defining the current breathing cycle differ from the corresponding values defining the reference breathing cycle. Each of these conditions may be indicative of the hazards such as disconnection of part of the patient breathing circuit, interruption of the patient's breathing gas, blockage of the patient breathing circuit, or a change in the physiological status of the patient, any of which may require attention. The conditions under which these alarms are produced, and the message texts associate with them, are described below.

The message texts "MAX PRESSURE>REFERENCE" or "MAX PRESSURE<REFERENCE" are displayed, as appropriate, on display 58 upon detection of a maximum pressure in any active breathing cycle which differs, by more than about 13 percent, from the maximum pressure of the reference breathing cycle.

The message texts "MIN PRESSURE>REFERENCE" or "MIN PRESSURE<REFERENCE" are displayed, as appropriate, on display 58 upon detection of a minimum pressure in any active breathing cycle which differs, by more than about 17 percent, from the minimum pressure of the reference breathing cycle.

The message texts "PERIOD>REFERENCE" or "PERIOD<REFERENCE" are displayed, as appropriate, on display 58 upon detection of any active breathing cycle having a period which differs by more than about 17 percent, from the period of the reference breathing cycle.

The message texts "AVERAGE PRESSURE>REFERENCE" or "AVERAGE PRESSURE<REFERENCE" are displayed, as appropriate, on display 58 upon detection of any active breathing cycle having an average pressure which differs, by more than about 17 percent, from the average pressure of the reference breathing cycle.

The message texts "I/E>REFERENCE" or "I/E<REFERENCE" are displayed, as appropriate, on display 58 upon detection of any active breathing cycle during which the I/E ratio differs by more than about 25 percent from the same ratio for the reference breathing cycle.

V. Construction and Technical Operation

(a) Pressure Sensing Means

Figure 5:
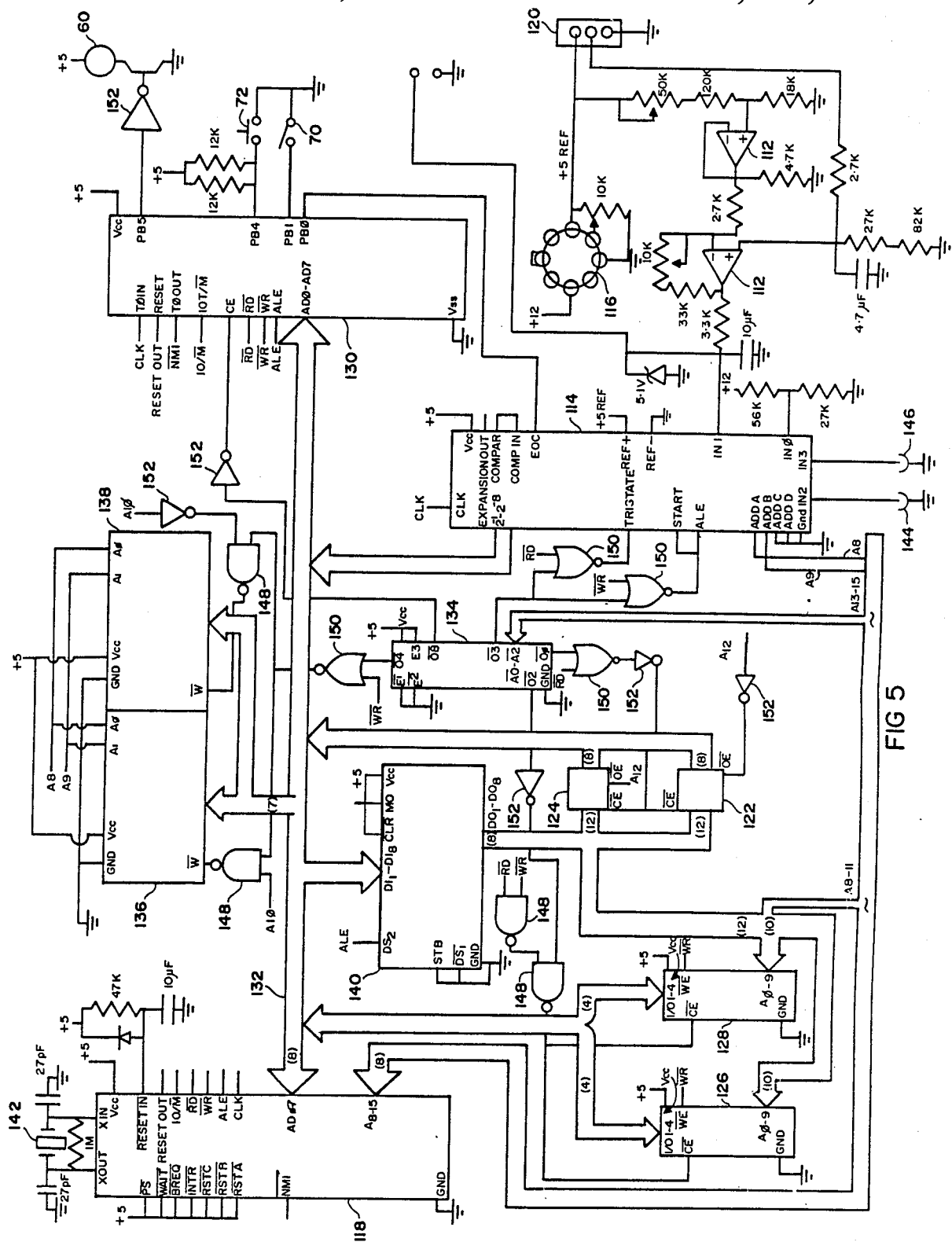
FIG. 5 is a electronic circuit schematic diagram for the microprocessor and related circuitry which controls the apparatus of the preferred embodiment, but does not include circuity for the optional modified gas monitor and its associated signal processing means.
Figure 6A:
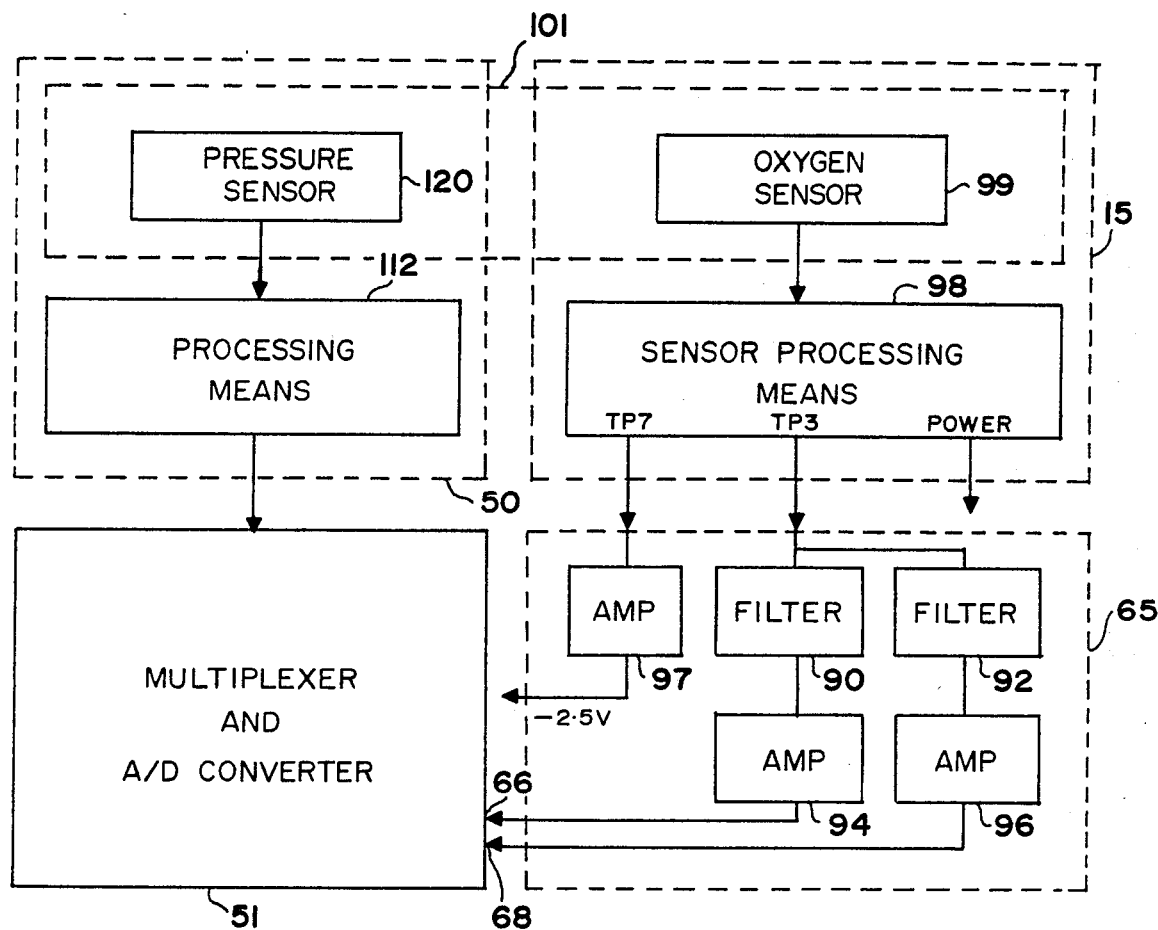
FIG. 6A is a block diagram of the optional modified gas monitor and its associated signal processing means.

In the preferred embodiment, pressure sensing means 50 is a Motorola MPX80MD pressure transducer 120 shown in FIG. 6A, together with amplifying and signal conditioning circuitry. The inlet to transducer 120 is connected directly to hose 52, which transmits the pressure in the patient breathing circuit to a pressure sensitive element within transducer 120. Transducer 120 produces a output voltage in the range of 0 to 5 volts which corresponds to gauge pressures of $-38$ to $+813$ $cmH_2O$. In the preferred embodiment, the pressure range used is $-12$ to $+52$ $cmH_2O$, corresponding to the range of pressure that might conceivably occur in a patient breathing circuit. This pressure range corresponds to a voltage range of 0.51 to 1.03 volts. A dual low power operational amplifier comprised of a National LM358 integrated circuit 112 shifts and scales the output of pressure transducer 120 by removing the 0.51 volt offset and by amplifying the pressure transducer output by a factor of 9.6 for presentation to analog to digital converter 114 (FIG. 5). The amplification factor is set to 9.6 in order to produce a signal that ranges over the entire 0 to 5 volt input range of the analog to digital converter, for pressures in the range of $-12$ to $+52$ $cmH_2O$.

In the preferred embodiment, analog to digital converter 114 is an eight-bit, 16-channel National ADC0816 integrated circuit. A voltage reference comprising a National REF02 integrated circuit 116 provides a standard reference for analog to digital converter 114, as well as a standard reference for pressure transducer 120.

(b) Microprocessor and Digital Circuity

Microprocessor 118 which monitors the patient breathing circuit pressure, triggers the alarms, drives the displays, etc. is a National Semiconductor NSC800 CMOS microprocessor. Two Intel 2732 4K × 8-bit electronically programmable read only memory ("EPROM") integrated circuits 122 and 124 store the logic program (hereinafter described under the heading "Software") which defines the sequence of operations by which microprocessor 116 functions. Two National 6514 1K × 4-bit static random access memory ("RAM") integrated circuits 126 and 128 serve as a "scratch pad" memory in which volatile data is stored.

A National NSC810 integrated circuit I/O device 130 provides two I/O ports, a timer and an additional 256 × 8 bits of static RAM.

A 30-line system bus 124 is used to pass information between microprocessor 118 and the various electronic devices with which it must communicate. Data and address information is passed in eight bit multiplexed format on lines AD0 through AD7. Lines A8 to A15 are used to pass an additional eight bits of addressing information. The IO/$\overline{M}$ line and address lines A13 through A15 are used by National 74PC138 decoder integrated circuit 134 to identify which of EPROMs 122 or 124, RAMs 126 or 128, I/O device 130, analog to digital converter 114 or displays 136 or 138 are being addressed by microprocessor 118.

Address latch 140, an Intel 82PC12 eight bit latch integrated circuit, demultiplexes the address information on lines AD0 through AD7, using timing information provided by microprocessor 118 on the ALE line. Demultiplexed address information is required for proper operation of EPROMs 122 and 124, and RAMs 126 and 128.

A 2.00 MHz quartz crystal 142 serves as a master clock for microprocessor 118, as well as a timing standard for the timer included in I/O device 130. The CLK line of bus 132 carries a frequency reference derived from crystal 142 to I/O device 130 and to analog to digital converter 114.

The remaining lines of bus 132 carry timing information to the various electronic devices connected to the bus. The reset line provides a signal to reset I/O device 130 when the power is turned on. The $\overline{RD}$ line is used by microprocessor 118 to indicate that it expects to read information from lines AD0 through AD7. The $\overline{WR}$ line is used by microprocessor 118 to indicate that it expects to write data to lines AD0 through AD7.

The non-maskable interrupt ($\overline{NMI}$) line of bus 132 carries a signal from the timer section of I/O device 130 to microprocessor 118. This signal forces microprocessor 118 to execute, at selected time intervals, an "interrupt service routine" called "trap", (hereinafter described under the heading "Software") which is stored in EPROMs 122 and 124.

The input/output device addresses are defined as follows:

| LINE | | | |
|---|---|---|---|
| A15 | A14 | A13 | DEVICE |
| 0 | 0 | 0 | EPROMs 122 and 124 |
| 0 | 0 | 1 | I/O Device 130 |
| 0 | 1 | 0 | RAMs 126 and 128 |
| 0 | 1 | 1 | Analog to digital converter 114 |
| 1 | 0 | 0 | Displays 136 and 138 |

The scaled and amplified output of pressure transducer 120 is presented to analog to digital converter 114 at its input terminal IN1 (input 1). Channel 0 of analog to digital converter 114 is connected through a resistor divider network to battery 64 so that the battery voltage can be monitored. Inputs IN2 and IN3 are connected to external signal input jacks 144 and 146 respectively. Microprocessor 118 is programmed to apply appropriate signals at the start and address latch enable terminals of analog to digital converter 114 to cause it to convert the pressure transducer, battery, or external input signals from analog to digital form. The converted eight-bit digital result is passed from analog to digital converter 114 to microprocessor 118 on lines AD0 through AD7.

I/O device 130 generates a signal for triggering audible alarm 60, and also reads in information from user control panel 62. These signals are conveyed as follows on lines PB0-PB7:

| LINE | DIRECTION | FUNCTION |
|---|---|---|
| PB0 | input | end of conversion from analog to digital converter 114 |
| PB1 | input | mode switch 70 |
| PB4 | input | alarm suppress switch 72 |
| PB5 | output | audible alarm 60 |
| PB2,3 | | |
| PB6,7 | | |

Displays 136 and 138 are two Litronix DL1416 intelligent alpha-numeric displays. There displays decode information presented to them on lines AD0 through AD6 of system bus 132 to provide a complete set of alpha-numeric characters. Address lines A8 and A9 are used to select which of the four characters within each display is to be written to by microprocessor 118. Alpha-numeric information is passed by microprocessor 118 in standard seven-bit ASCII format.

Integrated circuits 148, 150 and 152 comprising respectively a National 74PC00 quad 2-input NAND gate, a National 74PC02 quad 2-input NOR gate and a National 74PC04 hex inverter, provide miscellaneous logic functions needed to fully decode addressing information generated by microprocessor 118 for presentation to the various electronic devices connected to bus 132.

(c) External Pressure Sensing Means

Figure 6B:
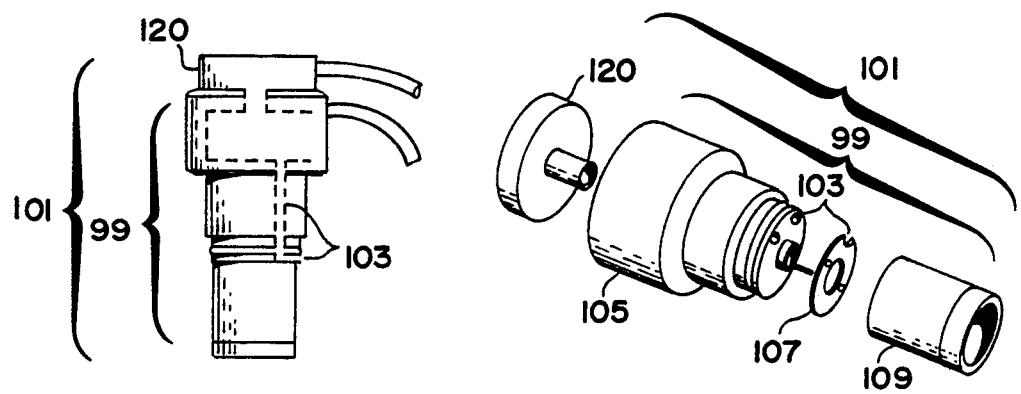
FIG. 6B is a pictorial representation of an integrated pressure and gas sensor which may be used with the optional modified gas monitor.
Figure 6C:
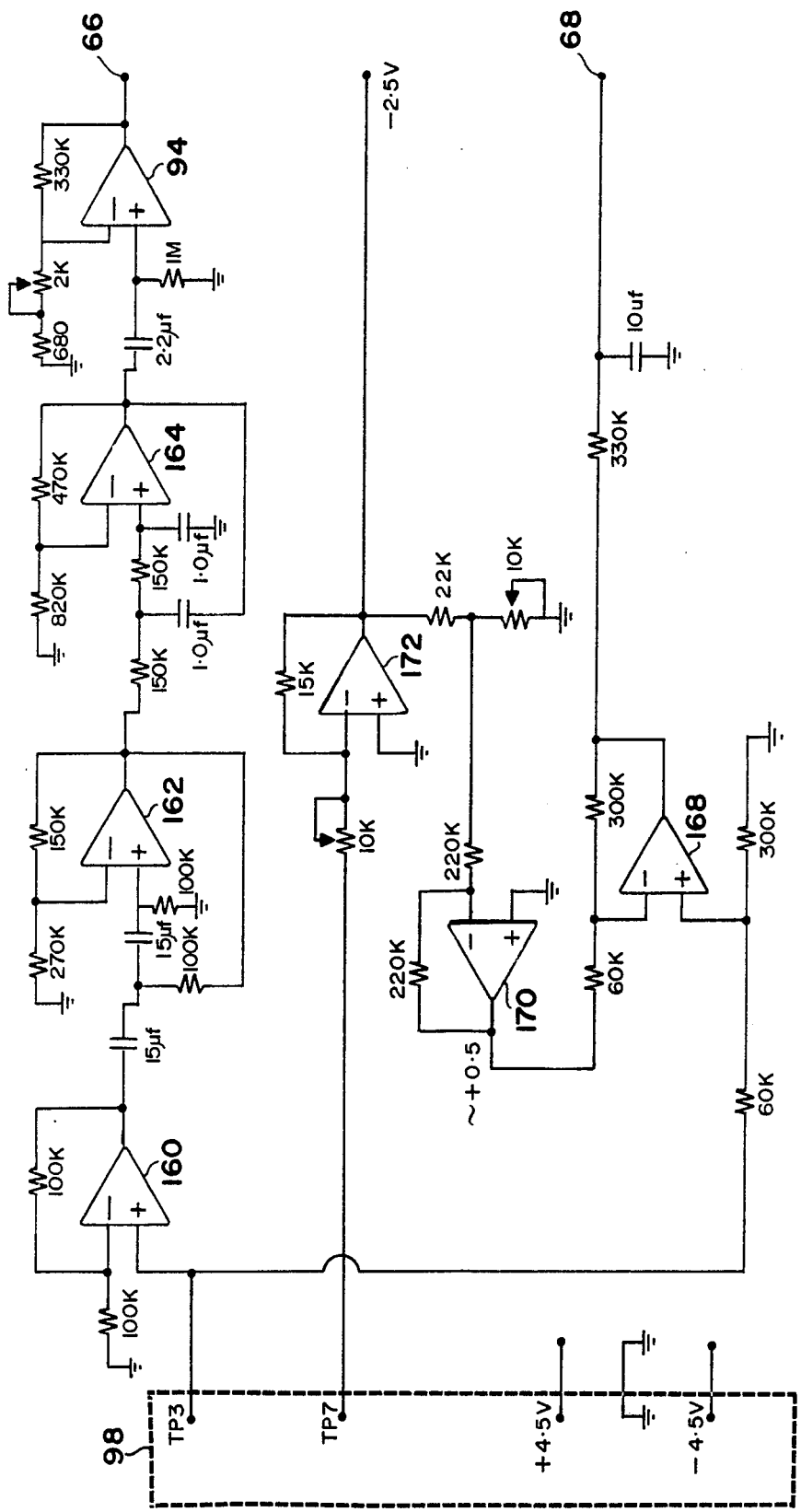
FIG. 6C is an electronic circuit schematic diagram for the circuitry of the signal processing means associated with the optional modified gas monitor.

In the preferred embodiment, gas monitor 15 is comprised of a modified Critikon Oxychek ™ oxygen analyzer having a Clark-type polarographic cell. FIG. 6A shows a block diagram of the modified oxygen analyzer including signal processing means 65, which has been designed for a breathing gas containing 21 percent oxygen and for a specific inspiratory flow pattern. FIG. 6B shows how oxygen sensor 99 of gas monitor 15 and pressure sensor 120 of pressure sensing means 50 may be conveniently combined as an integrated sensor. FIG. 6C illustrates the circuity of signal processing means 65. Signal processing means 65 contains bandpass filter 90 designed to pass frequencies in the range of 0.05 to 1.0 Hz, lowpass filter 92 designed to pass frequencies less than 0.3 Hz, amplifier 94 designed to amplify the output of bandpass filter 90 by a factor ranging from 500 to 2000 times, and amplifier 96 designed to amplify the output of lowpass filter 92 by a factor of five times. Also included in signal processing means 65 is a reference ground amplifier 97 designed to provide an adjustable DC offset to the signals from amplifiers 94 and 96.

As shown in FIG. 6A, gas monitor 15 in the preferred embodiment consists of an oxygen sensor 99 and sensor processing means 98. Similarly, pressure sensing means 50 in the preferred embodiment consists of pressure sensor 120 and processing means 112. Sensor 99 and sensor 101 may be an integrated sensor 101 as shown in FIG. 6B. In order to fabricate integrated sensor 101, a hole must be drilled through sensor head 105, and a notch must be made in washer 107 which is situated between sensor head 105 and sensor element 109. The hole and notch provide a passage 103 whereby pressure sensor 120 communicates with the pressurized gas in the patient breathing circuit at the normal location of the oxygen sensor 99. The integrated sensor 101 simplifies connections to the patient breathing circuit, assures that pressure dependent signals from both sensors 99 and 120 are obtained from the same location in the patient breathing circuit and facilitates the comparative analysis of signals derived from both sensors by microprocessor 118.

FIG. 6C shows the detailed circuitry of signal processing means 65 which, in the preferred embodiment, is physically located on a circuit board inside the gas monitor 15. Bandpass filter 90 consists of three sections of a National Semiconductor LM324 quad operational amplifier. The first section 160 is used as a pre-amplifier with a fixed gain of two. The second section 162 is used as a highpass filter. The third section 164 is used as a lowpass filter. There is a combined gain of two in the two filter sections.

Amplifier 94 consists of one section of a National Semiconductor LM324 quad operational amplifier, and is connected to provide a variable amplification factor ranging from 125 to 500 times. The output of amplifier 94 is connected to external input 66.

Lowpass filter 92 consists of two sections 168 and 170 of a national Semiconductor LM324 quad operational amplifier. The first section 168 acts as a pre-amplifier for the lowpass filter consisting of a resistor and capacitor network. The second section 170 acts as voltage reference for removing any offset that might be present at the input of amplifier 168.

Reference amplifier 97 comprises one section of a National Semiconductor LM324 quad operational amplifier 172. A reference voltage taken from Test Point 7 (TP7) of sensor processing means 98 provides a standard for this amplifier.

The signal from Test Point 3 (TP3) of signal processing means 98 is presented to the inputs of both bandpass filter 90 and lowpass filter 92. It is from this signal that pressure and gas concentration information detected by gas monitor 15 are derived. Electrical power to operate circuitry 65 is also derived from signal processing means 98 in gas monitor.

VI. Software

Appendix "A" to this specification is a 31 page source code listing for a computer program developed for the preferred embodiment. The computer program is written in the "C" programming language. The program was cross-compiled from the "C" programming language into 8080 machine language code acceptable to the National Semiconductor NSC800 microprocessor integrated circuit used in the preferred embodiment. This microprocessor has as its instruction set a superset of the instructions for the well known 8080 microprocessor integrated circuit and so the cross-compiled code could be run on the NSC800 microprocessor.

Although it is believed that the computer program listing, together with the comments embedded therein, should enable those skilled in the art to understand the operation of the computer program, a brief overview of the operation of the computer program is hereinafter provided.

Execution of the computer program begins with the routine named "_main()". The "main" routine calls a subroutine named "initialize()" which starts the timer section of I/O device 130 and causes it to generate a signal every one-tenth of a second. This signal used to cause microprocessor 118 to execute the subroutine "trap()" every one-tenth of a second, regardless of the present state of the program. The routine "initialize()" also turns on audible alarm 60 and displays the message "*O*O*O*" as part of the self-test procedure.

Upon completion of the "initalize()" routine, the program returns to the routine "main()" and enters an endless loop within which all further routines are coordinated. At the beginning of each cycle of the loop, the condition of external inputs 66 and 68 are checked to see if external signals have been applied. If no such signals are present, the program displays the message "NO O2 ANALYSER". This terminates the self-testing function.

During the execution of all routines coordinated by the routine "main", and hence during the entire time the program is running, the timer within I/O device 130 which was programmed and started in the routine initialize causes the microprocessor to execute the interrupt service routine "trap()" every one-tenth of a second. The routine trap causes a new value of pressure as detected by pressure transducer 120 to be read each time the routine is executed, as well as reading the battery voltage and the condition of both external input signals. In addition, the routine "trap" detects the operation of switches 70 and 72, and operates several timers used by other routines in the program. Before program control is returned to the interrupted routine, "trap" executes the subroutine "check()".

The subroutine "check" compares the latest reading of patient breathing circuit pressure, battery voltage, and the status of external signals with some absolute criteria. If any of these criteria are not met, the routine "check" causes an alarm. Program control is then returned to the interrupted routine.

Then the self-test procedure is complete, the routine "main" displays the message "READY" and waits for the operator to activate the "mode" switch 70. If an excessive period of time passes without the operator responding, the message "PRESS STORE NEW DATA WHEN READY" is displayed.

When mode switch 70 has been activated by the operator (as detected by the rountine "trap"), the routine "main" executes the rountine "learn()".

The routine "learn" begins by averaging the pressure readings detected by "trap" for ten seconds. This average pressure is stored in the variable designated ref.-cump. If an external signal is present, the pressure signal is averaged and stored in the variable oref.cump. Throughout the program, variables preceded with the letter "o" refer to information derived from external signal inputs.

When an average pressure is obtained, the routine "learn" executes the routine "readcycle". "Readcycle" uses the average pressure stored in the variable ref.-cump. to detect the beginning of either the expiratory or inspiratory phase of the patient breathing cycle. The routine then continues to use pressure valves read by the routine "trap" to detect the maximum pressure, minimum pressure, average pressure, inspiration time and expiration time that characterizes the breathing cycle. Before returning to the calling routine, "readcycle" calculates the total period and I/E ratio of the breathing cycle. If the I/E ratio is greater than or less than certain limits, "readcycle" displays appropriate warning messages and activates the audible alarm.

When program control returns to the routine "learn" from the routine "readcycle", the values of maximum pressure, minimum pressure, average pressure, I/E ratio and total period are stored in the variable structures ref and oref. The routine "readcycle" is executed again, and the resulting breathing cycle characteristics are compared to those stored in the ref and oref structures by the routine "compare".

The routine "compare" uses the routine "normalize" to calculate the percent difference between the current breathing cycle data (stored in the structures cur and ocur) and the reference data stored in the ref and oref structures. If all the comparisons fall within the percentage limits passed to the routine "compare" by the calling routine, control is returned directly to the calling routine. If any of the comparisons fail, a message is displayed and the audible alarm is sounded.

When program control is returned to the routine "learn" from the routine "compare", the routine "learn" will, if all comparisons made by the routine compare caused no alarm conditions, average the values stored in the ref and oref structures with those in the cur and ocur structures to define a "reference breathing cycle". If execution of the routine "compare" resulted in the generation of an alarm condition, the routine "readcycle" is called again to obtain a third referential breathing cycle. Further cycles are obtained until the routine "compare" is executed without the generation of an alarm condition, or until an excessive number of breathing cycles have been obtained without any two consecutive cycles matching with the constraints of the routine "compare", at which time an appropriate message is displayed and the audible alarm is sounded.

When the routine "learn" is completed, the routine "main" executes the routine "test". The routine "test" immediately enters a loop that is not exited until the operator presses mode switch 70 to cause the microprocessor to "learn" a new reference breathing cycle. Within the loop, the routine "test" simply calls "readcycle" and "compare" in succession, hence causing alarms to be activated whenever there is an unacceptable difference between the reference information and the current information determined by the routine "readcycle". The routine "test" also checks to see if the operator has activated the "calibrate" mode of operation, and if so, calls the routine "calibrate".

The routine "calibrate" takes the values of pressure determined by the routine trap and displays them on the alpha-numeric display. The routine "translate" is used to convert the binary numbers generated by analog to digital converter 114 into ASCII code for presentation to displays 136 and 138. "Calibrate" also checks the status of the mode switch 70 to determine if the operator wishes to proceed to the next sub-mode of the calibration mode. Each time the mode switch is activated, the routine calibrate begins displaying another of the signals sensed in the routine trap. When the mode switch is activated a fourth time, the first sub-mode of the calibrate mode, displaying pressure information, is activated again. When the calibration mode is terminated by the operator, program control returns to the calling routine.

If the routine test is terminated by the operator through activation of the mode switch 70, program control is returned to the routine "main", which begins executing the loop again, starting with the self test to determine if external signal sources have been connected.

In addition to the routines already described, there are four routines that are used by several other routines to execute particular functions. The routine "alarm" is used to determine which of several simultaneous alarms should be given priority. The routine "billb" causes the current message to be displayed, and provides a rotating billboard effect for messages that are too long for the eight-character display. The routine "adcmn" is used to start the analog to digital converter in order to obtain a new value for the selected input signal. The last routine, "sense", is used to cause a new value of pressure to be read and added to a running total pressure for averaging purposes. The routine sense also stores the maximum and minimum pressure values encountered during successive executions of the routine.

As will be apparent to those skilled in the art, in light of the foregoing disclosure, many alterations and modifications are possible in the practice of this invention without departing from the scope or spirit thereof. For example, the circuitry and software associated with the external pressure sensing means could be modified to accommodate breathing gas containing different percentages of oxygen and various inspiratory flow patterns. As another example, modifications may be made which would facilitate use of the invention with high frequency ventilators. Accordingly, the scope of the invention is to be construed in accordance with the substance defined by the following claims.

APPENDIX A

1

```
/***************
** MAIN.DPM   *
****************
*
*   The routine _main() calls the initialization subroutine, checks to
*       see if an oxygen analyser is connected to the AUX input, waits
*       for the learn switch to be pressed, and then calls the learn
*       and test subroutines. If the learn switch is not pressed
*       within a given number of interrupts, an alarm message will be
*       displayed.
*
*       THIS ROUTINE CALLS:    initialize()
*                              alarm()
*                              billb()
*                              learn()
*                              caltest()
*                              test()
*
*       GLOBALS:   All program globals are defined in this routine.
*                  The following globals are used by the routine _main():
*              alm_counter  = US = number of interrupts left for alarm on
*              relearn      = UC = 1 just after learn switch is pressed
*                                  0 otherwise
*              rout_count   = US = counter which decrements on each
*                                  interrupt until learn mode is entered.
*                                  If rout_count == 0 than an alarm
*                                  message is displayed.
```

```
*           status        = UC = boolean variable which indicates
*                                whether data is being processed.
*           state         = US = indicates which part of the algorithm
*                                is presently being executed. state == 0
*                                refers to ready mode and prevents the
*                                checking for low pressure, and long
*                                period.
*           message       = UC = pointer to current message.
*           calibrate     = US = flag which == 1 if calibrate mode has been
*                                selected by the operator, == 0 otherwise.
*           omonitor      = US = flag which is set == 1 if an oxygen analyser
*                                is connected to the aux input.
*
*
*     STATIC LOCALS:  none used
*
*     AUTOMATIC LOCALS:  none used
*
*     ARGUMENTS:  none used
*
*     CONSTANTS:  All program constants are defined in this routine.
*                 The following constants are used in the routine _main():
*           LRN_TIM       = time allowed to press 'learn' key.
*
***********************************************************************/
#include "DLO:STD.H"
#define ADCV           0x60          /* port definitions for A/D converter */
#define ADCX           0x61
#define ADC2           0x62
#define ADC3           0x63
#define ALM_OFF        0xDF          /* bit masks for I/O port */
#define ALM_ON         0x20
#define ASP_OFF        0x10
#define ASUPPRESS      300           /* constants for program operations */
#define AVG_HYS        0x04
#define AVG_START      20
#define AVG_TIME       100
#define BASE_P         0x00
#define BAT_CRITICAL   0xA0
#define BAT_LOW        0xB4
#define BAT_OFFSET     0xC7
#define CMD            0x01
#define CMDREG         0x20
#define DISPLAY        0x87
#define DISPTIM        24000
#define E_DIFF         20
#define HIGH_LIMIT     800
#define I_DIFF         20
#define INIT_STAT      0x01
#define LOW_LIMIT      100
#define LRN_PERCENT    10
#define LRN_NUM        10
#define LRN_OFF        0x02
#define LRN_ON         0xFD
#define LRN_TIM        1200
#define MAX_IOE        256
#define MIN_IOE        12
#define MIN_LIMIT      10
#define NOPRESTIME     150
#define NO_PRES_DIFF   0x14
#define MAX_PERIOD     300
#define MAXMES         35
#define P_MAX          180
#define P_MIN          32
#define P_OFFSET       48
#define PA             0x20          /* port addresses and command registers */
#define PB             0x21
#define PSLOPE         0x06
#define START_TIMER    0x35
#define STOP_TIMER     0x34
```

```
#define TEST_PERCENT    6
#define TIM             0xFF
#define TIMCMD          0x1E
#define TIML            0x1A
#define TIMH            0x06
#define GAIN            45

/* Global variable definitions */ struct
    begin
        unsigned char rev_message[MAXMES+16];
    end;
define rmes (0x4000->rev_message)                   /* message structure */ unsigned char *message = 0;
unsigned short greater = 0;
unsigned short state = 0;
unsigned short avg_count = 0;
unsigned short length = 0;
unsigned short learn_count = 0;
unsigned short alm_counter = 0;
unsigned short rout_count = 0;
unsigned short alm_priority = 0;
unsigned short osavelevel = 0;
unsigned short learnflag = 0;
unsigned short calibrate = 0;
unsigned short window = 0;
unsigned short trap_cnt = 0;
unsigned char porta = 0;
unsigned char portb = 0;
unsigned char ptb = 0;
unsigned char status = 0;
unsigned short condition = 0;
unsigned short sup_count = 0;
unsigned char error_type = 0;
unsigned short p = 0;
unsigned short opress = 0;
unsigned short olevel = 0;
unsigned short omonitor = 1;
unsigned short percent = 0;
unsigned short ins = 0;
unsigned short oins = 0;
unsigned short exp = 0;
unsigned short oexp = 0;
unsigned short bat = 0;
unsigned char relearn = 0;

struct
    begin
        unsigned short per;
        unsigned short iovere;
        unsigned short cump;
        unsigned short minp;                  /* breathing cycle data structures */
        unsigned short maxp;
    end ref=0, cur=0, oref=0, ocur=0;

/* Files linked to this program */ include "DL1:TRAP.DPM"
include "DL1:INIT.DPM"
#include "DL1:BILLB.DPM"
#include "DL1:ADCMN.DPM"
#include "DL1:LEARN.DPM"
#include "DL1:TEST.DPM"
#include "DL1:READC.DPM"
#include "DL1:ALARM.DPM"
#include "DL1:CHECK.DPM"
#include "DL1:COMPAR.DPM"
#include "DL1:TRANS.DPM"
```

```
#include "DL1:CAL.DPM"
#include "DL1:NORM.DPM"
#include "DL1:SENSE.DPM"

/* Actual program execution begins here */

_main()
begin
    initialize();
    for (;;)                                /* this loop is executed forever */
    begin
        rout_count = LRN_TIM;     /* sets time limit for operator to activate */
        while (alm_counter)                 /* allows self-test mode to finish */
           status = 0;
        if (!omonitor)                      /* if no O2 analyser connected */
          begin                             /* display message               */
             message = "NO O2 ANALYSER";
             alarm (5);
             alm_counter = 34;              /* limits time that alarm is active */
          end
        learnflag = 0;                                  /* zero flags */
        calibrate = 0;
        while ( !relearn )          /* wait for learn switch to be prssed */
        begin
            status = 0;
            state = 0;
            while ( !status )       /* wait for interrupt. status is set   */
              ;                     /* =1 by the interrupt routine trap()  */
            if ( !alm_counter )         /* as long as there is no alarm,   */
            begin                       /* display the message.            */
               message = "READY";
               billb();
            end
            if ( !rout_count )          /* if too long without learning,   */
            begin                       /* display message                 */
                message = "PRESS \"STORE NEW DATA\" WHEN READY";
                alarm(10);
                rout_count = LRN_TIM;
            end
            if (calibrate) caltest();
        end
        alm_counter = 0;
        learn();
        test();
        status = 0;
        while ( relearn )
           ;
    end
end
/**/
/**/
rst75()
begin
end /*****************
**   INIT.DPM    *
******************
*
*  The routine initialize() initializes global variables, the timer
*     registers of the NSC810, and the input/output select registers
*     for port B on the 810. The self-test message is displayed on the
*     display and timer 0 on the 810 is started.
*
*     THIS ROUTINE CALLS: out()
*                         alarm()
*
*     GLOBALS:
*         status       = UC = boolean variable which indicates whether
*                             CPU is busy.
*         learn_count  = US = number of breathing cycles left in which to
*                             learn a reference cycle.
```

```
*         relearn       = US = flag that indicates mode switch pressed
*         alm_counter   = US = number of interrupts left with alarm on
*         alm_priority  = UC = priority of current alarm
*         greater       = US = flag used to set > or < sign in messages
*         sup_count     = US = number of interrupts left during which
*                              alarm is to be suppressed
*         state         = US = 1 during pressure averaging
*                              2 during learning and testing of cycles
*         portb         = UC = the contents of port B
*         message       = UC = character string of display string.
*
*     STATIC LOCALS: none used
*
*     AUTOMATIC LOCALS: none used
*
*     ARGUMENTS: none used
*
*     CONSTANTS:
*         TIML          = low order byte of timer 0
*         TIMCMD        = timer command information
*         TIMH          = high order byte of timer 0
*         START_TIMER   = timer 0 start address
*
*************************************************************************/ initialize()
begin
    status = 1;
    out(0x25,0xE0);                          /* assign input/output to port B */
    out(0x38,TIMCMD);                        /* timer 0 mode */
    out(0x30,TIML);                          /* lower byte of timer */
    out(0x31,TIMH);                          /* upper byte of timer */
    learn_count = alm_priority = greater = 0;
    sup_count = relearn = state = 0;
    portb = 0xFF;
    message="*0*0*0*0*0";                    /* tests all segments of display */
    alarm(1);
    alm_counter = 18;
    out(START_TIMER,0);                      /* start timer */
end /***************
* TRAP.DPM     *
***************
*
* The routine trap() performs the maintenance of alarm conditions
*     and messages, checks the MODE and ALARM RESET switches, and
*     then reads a new pressure point and battery voltage value.
*     Trap() is called on each non-maskable interrupt generated by
*     timer 0 on the NSC810. If this routine is called before
*     processing of the previous point is complete the message
*     MALFUNCTN will be displayed, and monitoring of the breathing
*     circuit pressure is terminated. Trap also checks to see if an
*     oxygen analyser is connected to the aux input, and if so, sets
*     omonitor == 1.
*
*     THIS ROUTINE CALLS: out()
*                         billb()
*                         in()
*                         adcmn()
*                         check()
*
*     GLOBALS:
*         message       = PT = pointer to the current message
*         status        = UC = boolean variable which indicates whether
*                              CPU is busy.
*         alm_counter   = US = number of interrupts left for alarm on
*         portb         = UC = latest contents of port B on 810
*         alm_priority  = US = priority of current alarm condition
*         learn_count   = US = number of breathing cycles left to
*                              learn a reference cycles
```

```
*              window         = US = leftmost character in portion of message
*                                    currently being displayed
*              relearn        = US = flag set when mode switch pressed
*              calibrate      = US = flag set when calibrate mode selected
*              omonitor       = US = flag set when O2 analyser connected
*              trap_cnt       = US = counter incremented on each interrupt
*              length         = US = length of latest message
*              rmes           = PT = pointer to the array rev_message
*              sup_count      = US = number of interrupts left for audio
*                                    alarm suppress
*              ptb            = UC = temporary location for latest input
*                                    from port B.
*              rout_count     = US = counter which decrements on each
*                                    interrupt
*              p              = US = latest pressure reading
*              bat            = US = latest battery voltage reading
*              opress         = US = pressure reading as detected by O2 analyser
*              olevel         = US = O2 concentration as detected by O2 analyser
*              avg_count      = US = counter decremented on each interrupt
*              learnflag      = US = counts the number of times relearn has
*                                    been activated while the alarm suppress
*                                    switch is held.  If learnflag == 2 in
*                                    the presence of an alarm, relearn is set
*                                    to 1 to allow relearning.  If learnflag == 3
*                                    then caltest() will be executed as soon as
*                                    possible.
*
*     STATIC LOCALS: none used
*
*     AUTOMATIC LOCALS:
*         count          = US = counter used in displaying new message
*                               window
*
*     ARGUMENTS: none used
*
*     CONSTANTS:
*         STOP_TIMER     = port number of register to stop timer 0
*         PB             = port number corresponding to port B on 810
*         ALM_OFF        = mask to turn audio alarm off
*         DISPLAY        = port number addressing rightmost character
*                          in alphanumeric display
*         ALM_ON         = mask to turn audio alarm on
*         LRN_OFF        = mask to determine if MODE switch pressed
*         ASP_OFF        = mask to determine if ALARM RESET switch
*                          pressed
*         ASUPPRESS      = number of interrupts that audio alarm will be
*                          suppressed
*         ADCX           = port number to start A/D conversion of
*                          pressure
*         ADCV           = port number to start A/D conversion of
*                          battery voltage
*         ADC2           = port number to start A/D conversion of
*                          pressure detected by O2 analyser
*         ADC3           = port number to start A/D conversion of
*                          concentration detected by O2 analyser
*
***********************************************************************/
trap()
begin
unsigned short count;
    if ( status && (!relearn))      /* if status is == 1, last interrupt never */
    begin                            /* finished processing, hence a malfunction*/
       message = "MALFUNCN";         /* has occurred.                           */
       alarm(127);
       out(STOP_TIMER,0);
       for (;;)                                   /* stop everything and do nothing */
          ;
    end
    status = 1;
    if ( alm_counter )  --alm_counter;
```

```
if ( !alm_counter )                             /* provided no alarms are active */
begin
    out(PB,portb &= ALM_OFF );                  /* turn off the audible alarm */
    alm_priority = 0;
    if (learn_count)                            /* if in learn mode, display message */
    begin
        message = "LEARNING";
        billb();
    end
end
else                                            /* if there is an active alarm */
begin
    if (window && (trap_cnt & 0x01) )           /* allow only on every 2nd trap */
    begin
        if (window >= length) window = 1;       /* move to appropriate part of */
            else ++window;                      /* the message and display it. */
        for (count = 0; count <= 7; count++)
            out(DISPLAY - count, rmes[window+count]);
    end
    if ( !sup_count ) out(PB,portb |= ALM_ON);  /* if alarm supression on */
        else  out(PB,portb &= ALM_OFF);         /* turn alarm off.       */
end
ptb = in(PB);                                   /* read in port B */
if (!(ptb & ASP_OFF))                           /* if alarm supress switch is closed */
   begin
      if (portb & ASP_OFF)                      /* if alarm supress switch was just pushed */
         sup_count = ASUPPRESS;                 /* supress alarm */
      if ((portb & LRN_OFF) && (!(ptb & LRN_OFF))) /* if learn just pushed */
         ++learnflag;
      if ((learnflag == 2) && (alm_counter))
         begin
            status = 0;          /* second time learn switch pushed while alarm*/
            relearn = 1;         /* switch held closed, relearn.               */
         end
      if (learnflag == 3)        /* third time learn switch pushed while alarm */
         calibrate = 1;          /* switch held, calibrate.                    */
   end
else
/* if any alarm other than low pressure for 15 sec, do not allow relearn */
   if ((!alm_counter) || (alm_priority == 110))
      relearn = ((portb & LRN_OFF) && (!(ptb & LRN_OFF))) ? 1 : 0;
portb = ptb;                                    /* save new portb contents */
if (relearn) alm_counter =0;                    /* if relearn entered, defeat alarms */
if ( rout_count )  --rout_count;                /* various timers */
if ( avg_count )  --avg_count;
if ( sup_count )  --sup_count;
++trap_cnt;
p = adcmn(ADCX);                                /* make new readings of pressure */
bat = adcmn(ADCV);                              /* battery and aux inputs        */
opress = adcmn(ADC2);
olevel = adcmn(ADC3);
if (olevel > 8)                                 /* if aux input non zero, assume */
   omonitor = 1;                                /* that an O2 analyser is connected*/
else
   omonitor = 0;
check();                                        /* check against absolute limits */
end /***************
*  CHECK.DPM   *
***************
*
*  The routine check(), will compare the current battery voltage
*       and pressure point against absolute criteria and generate an
*       alarm condition if something inappropriate has occured.
*
*       THIS ROUTINE CALLS: alarm()
*
*       GLOBALS:
*               bat       = US = current battery voltage conversion.
*               p         = US = current pressure converison.
```

```
*              message       = PT = pointer to current message.
*              state         = US = 0 during ready state and pressure averaging
*                                   1 during learning
*                                   2 during testing of breathing cycles.
*              rout_count    = US = is decremented on each interrupt.
*              alm_priority  = US = priority of presently active alarm condition
*              alm_counter   = US = number of interrupts left for alarm on.
*              ins           = US = number of inspiratory points in last cycle
*              exp           = US = number of expiratory points in last cycle.
*              omonitor      = US = flag set if O2 analyser is connected.
*              olevel        = US = O2 concentration detected by O2 analyser.
*              trap_cnt      = US = incremented on each interrupt.
*
*       STATIC LOCALS: none used
*
*       AUTOMATIC LOCALS: none used
*
*       ARGUMENTS: none used
*
*       CONSTANTS:
*              STOP_TIMER   = port number of register to stop timer 0 on 810
*              BAT_OFFSET   = A/D reading corresponding to 12V.
*              BAT_CRITICAL = minimum battery voltage for proper operation
*              P_OFFSET     = A/D reading corresponding to atmospheric
*                             pressure
*              P_MAX        = A/D reading above atmospheric pressure which
*                             is considered to be high pressure.
*              P_MIN        = A/D reading below atmospheric pressure which
*                             is considered to be negative pressure.
*              MAX_PERIOD   = period length considered to be excessively
*                             long.
*              BAT_LOW      = battery voltage corresponding to 1 hour of
*                             remaining operation.
*
*****************************************************************************/
check()
begin
   if (bat < BAT_CRITICAL)       /* if battery voltage is too low, shut down. */
   begin
      message = "DEAD BATTERY - DPM OFF";
      alarm(127);
      out(STOP_TIMER,0);                       /* stop interrupt generation */
      for (;;)                                 /* do nothing */
         ;
   end
   else if ( p > (P_OFFSET + P_MAX) )     /* if pressure reading too high */
   begin
      message = "HIGH PRESSURE";
      alarm(120);
   end
   else if ( p < (P_OFFSET - P_MIN) )  /* if pressure less than zero level */
   begin
      message = "NEGATIVE PRESSURE";
      alarm(120);
   end
   else if ( (state) && (!rout_count) )   /* as long as not in READY state */
   begin                                  /* and time has run out for a    */
      message = "LOW PRESSURE FOR 15 SEC"; /* change in pressure           */
      if ( alm_priority == 110 )  alm_counter = 2;
         else    alarm(110);
   end
   else if ( ((ins + exp) > MAX_PERIOD) && ( state == 2 ) )
   begin
      message = "PERIOD > 30 SEC";     /* if period too long during testing */
      alarm(100);
   end
   else if ( ( bat < BAT_LOW ) && (!(trap_cnt & 0x07FF)) )
   begin
      message = "LOW BATTERY";    /* if battery low and 12.8 seconds passed */
      alarm(20);
   end
```

```
      else if ((olevel < 50 ) && (omonitor))
        begin
          message = "CHECK O2 SENSOR";      /* if O2 concentration < 20% and */
          alarm (16);                       /* analyser connected            */
        end
end
/***************
*   LEARN.DPM   *
****************
*
*   The routine learn() will read in pressure cycles until 2
*       consecutive cycles agree within approximately 10%. The
*       procedure compare() performs the actual comparison. When 2
*       consecutive cycles do agree the 2 cycles are averaged with
*       the average being stored in structure  ref . The routine
*       readcycle() does the actual cycle reading.
*
*       THIS ROUTINE CALLS:   alarm()
*                             sense()
*                             readcycle()
*                             compare()
*
*       GLOBALS:
*         rout_count  = US = decrements with each cycle until it reaches
*                            0 at which point the alarm is activated cor-
*                            responding to low pressure for 15 seconds.
*         message     = PT = pointer to display message.
*         relearn     = US = flag which indicates that MODE switch has
*                            been pressed.
*         status      = UC = boolean variable which indicates whether
*                            data is being processed.
*         learn_count = US = number of cycles left to find two consequtiv
*                            similar breathing cycles.
*         error_type  = UC = type of relative error:
*                            0 = no error
*                            1 = first cycle
*                            2 = second cycle
*                            >2 = relative error
*         ref         = ST = structure with reference pressure variables.
*         cur         = ST = structure with current pressure variables.
*         oref        = ST = structure with reference O2 pressure variables.
*         ocur        = ST = structure with current O2 pressure variables.
*         state       = US = 1 during pressure averaging
*                            2 during learning and testing of breathing
*                            cycles
*         avg_count   = US = number of pressure points to be averaged
*         learnflag   = US = counts number of times relearn is pressed while
*                            alarm supress switch is held
*
*       STATIC LOCALS:   none used
*
*       AUTOMATIC LOCALS:
*             pp   = US = difference between ref.maxp and ref.minp
*             opp  = US = difference between oref.maxp and oref.minp
*
*       ARGUMENTS:   none used
*
*       CONSTANTS:
*          LRN_NUM      = number of cycles without agreement before
*                         an error message appears.
*         NOPRESTIME    = number of interrupts before a low pressure
*                         alarm condition appears
*         LRN_PERCENT   = a number which is 100 / ( the maximum percent
*                         difference between the two cycles ).
*          AVG_TIME     = number of interrupts during which pressure is averaged
*             GAIN      = factor by which O2 peak to peak value must be multiped
*                         to compensate for the gain setting of the O2 analyser
*                         modification circuitry at 21% O2.
*
**************************************************************************/
```

```
learn()
begin
   unsigned short pp=0, opp=0;
   learnflag = 0;
   status = 0;                                       /* wait for an interrupt */
   while ( !status )
      ;
   if (!relearn)                           /* as long as relearn has not been pushed */
      begin                                /* again, start the learning process      */
         ref.cump = cur.cump = 0;
         cur.minp = 0xFF;
         oref.cump = ocur.cump = 0;
         ocur.minp = 0xFF;
         learn_count = LRN_NUM;
         avg_count = AVG_TIME;
         state = 1;
         while ( avg_count && ( ! relearn ) )
            begin                                    /* average the pressure for a time */
               ref.minp = cur.minp;                  /* to get a reference pressure     */
               sense();
            end
         ref.cump = cur.cump / AVG_TIME;          /* set up the reference pressure */
         oref.cump = ocur.cump / AVG_TIME;
         ref.minp = ref.cump;
         ref.maxp = ref.cump;
         oref.minp = oref.cump;
         oref.maxp = oref.cump;
         state = 2;
         rout_count = NOPRESTIME;
         readcycle();                              /* read a pressure cycle */
         error_type = 1;
      end
   while ( error_type && (!relearn))           /* as long as compare() keeps    */
      begin                                    /* giving errors, read new cycles */
         if ( ! (--learn_count) )
            begin                              /* if too many bad cycles, alarm */
               message = "INCONSISTENT CYCLES";
               alarm(80);
            end
         ref.per = cur.per;                    /* copy the characteristics */
         ref.iovere = cur.iovere;              /* from the most recent     */
         ref.minp = cur.minp;                  /* cycle ( ie. values in    */
         ref.maxp = cur.maxp;                  /* cur   structure ) into   */
         ref.cump = cur.cump;                  /* ref   structure.         */
         oref.per = ocur.per;                  /* copy the characteristics */
         oref.iovere = ocur.iovere;            /* from the most recent O2  */
         oref.minp = ocur.minp;                /* cycle ( ie. values in    */
         oref.maxp = ocur.maxp;                /* cur   structure ) into   */
         oref.cump = ocur.cump;                /* ref   structure.         */
         readcycle();                          /* read another cycle and test it out */
         compare(LRN_PERCENT);
      end
   ref.per = (ref.per + cur.per) >> 1;         /* average the last 2 learn */
   ref.iovere = (ref.iovere + cur.iovere)>>1;  /* cycles and store the     */
   ref.minp = (ref.minp + cur.minp) >> 1;      /* result in the  ref       */
   ref.maxp = (ref.maxp + cur.maxp) >> 1;      /* structure.               */
   ref.cump = (ref.cump + cur.cump) >> 1;
   oref.per = (oref.per + ocur.per) >> 1;
   oref.iovere = (oref.iovere + ocur.iovere)>>1;
   oref.minp = (oref.minp + ocur.minp) >> 1;
   oref.maxp = (oref.maxp + ocur.maxp) >> 1;
   oref.cump = (oref.cump + ocur.cump) >> 1;
   learn_count = 0;
   pp = (ref.maxp - ref.minp);                 /* calculate peak to peak   */
   opp = (oref.maxp - oref.minp);              /* values of pressure.      */
      if ((normalize((opp * GAIN),(pp * ref.per)) < 5) && (omonitor))
         begin
            message = "CHECK SENSORS";         /* if peak to peak output not equal */
            alarm (50);                        /* for O2 and internal pressure    */
         end                                   /* sensors, cross check fails      */
end
```

```
/***************
 *  READC.DPM  *
 ***************
 *
 *   The routine readcycle() will read a complete cycle beginning when
 *       the pressure crosses the mean level. After the end of the
 *       cycle has been reached, the I/E ratio is computed.
 *
 *   THIS ROUTINE CALLS:  out()
 *                        sense()
 *                        alarm()
 *
 *   GLOBALS:
 *               cur = ST = structure containing current pressure information
 *               ref = ST = structure containing reference pressure information
 *         osavelevel = US = temporary storage for the O2 concentration
 *             olevel = US = latest O2 concentration reading
 *                ins = US = number of inspiration points
 *                exp = US = number of expiration points
 *               oins = US = number of O2 cycle inspiration points
 *               oexp = US = number of O2 cycle expiration points
 *                  p = US = latest pressure reading
 *        alm_counter = US = number of cycles alarm is active
 *        learn_count = US = number of cycles left in learn
 *            relearn = US = flag = 1 if learn switch pressed, = 0 otherwise
 *           omoniter = US = flag = 1 if O2 analyser connected, = 0 otherwise
 *
 *   AUTOMATIC LOCALS:
 *             inspir  = UC = 0 if expiratory
 *                           1 if inspiratory
 *            oinspir  = UC = same, used for O2 cycle
 *             marker  = UC = number of times pressure has crossed mean
 *                           pressure level. Used to find end of cycle
 *            omarker  = UC = same, used to find end of O2 cycle
 *               flag  = UC = temporary storage for inspir
 *              oflag  = UC = same, used for O2 cycle
 *              savep  = US = temporary storage for cur.cump
 *             osavep  = US = temporary storage for ocur.cump
 *            average  = US = mean pressure storage
 *           oaverage  = US = mean O2 cycle storage
 *
 *   ARGUMENTS: none used
 *
 *   CONSTANTS:
 *       AVG_HYS = hysteresis used when checking for a transistion
 *                 from inspiratory to expiratory or vice versa.
 *       PB      = port number corresponding to port B register on
 *                 810
 *       LRN_NUM = number of cycles allowed to learn reference
 *                 cycle.
 *       MAX_IOE = 64 * maximum allowed I/E ratio.
 *       MIN_IOE = 64 * minimum allowed I/E ratio.
 *
 ***********************************************************************/ readcycle()
begin
unsigned char  marker=0, omarker=0, inspir=0, oinspir=0, flag=0, oflag=0;
unsigned short savep=0, osavep=0, average=0, oaverage=0;
cur.cump = ocur.cump = 0;
average = ((ref.maxp + ref.minp) >> 1);         /* calculate mean pressure */
oaverage = ((oref.maxp + oref.minp) >> 1);
osavelevel = olevel;                            /* save the initial O2 concentration */
ins = exp = 0;
oins = oexp = 0;
cur.maxp = ocur.maxp = 0;
cur.minp = ocur.minp = 0xFF;
if (p >(average + AVG_HYS)) flag = 1;           /* set initial value of flag */
if ((omonitor) && (opress > (oaverage + AVG_HYS))) oflag = 1;
   while ((!relearn) && ((marker < 3) || (omarker < 3)))
```

```
    begin                    /* do until both O2 and pressure cycles cross mean */
      sense();               /* value for the third time.                       */
      if ((p <(average - AVG_HYS)) && (marker < 3))
          inspir = 0;
      if ((p>(average + AVG_HYS)) && (marker < 3))
          inspir = 1;
      if (flag != inspir) then         /* if status of inspir has changed */
          begin                        /* then have crossed mean again    */
            ++marker;
            if (marker == 1)   /* if this is first mean crossing, initialize */
               begin
                  ins = 0;
                  exp = 0;
                  cur.cump = 0;
               end
            if (marker == 3) then    /* if third time, then cycle finished */
               begin
                  cur.per = ins + exp;             /* save values of cycle */
                  savep = cur.cump / cur.per;
                  cur.iovere = (ins << 6) / exp;
               end
          end
      flag = inspir;           /* store new status of inspir for next test */
      if (marker < 3)
         begin                 /* if not final cycle, increment number of  */
            if (inspir) then   /* inspiration or expiration points, as     */
               ++ins;          /* appropriate                              */
            else
               ++exp;
         end
      if(omonitor) then                            /* if O2 analyser connected */
         begin
            if ((opress <(oaverage - AVG_HYS)) && (omarker < 3))
                oinspir = 0;
            if ((opress>(oaverage + AVG_HYS)) && (omarker < 3))
                oinspir = 1;
            if (oflag != oinspir) then
               begin                                /* Exactly as above */
                  ++omarker;                        /* but for O2 cycle */
               if (omarker == 1)
                  begin
                     oins = 0;
                     oexp = 0;
                     ocur.cump = 0;
                  end
               if (omarker == 3) then
                  begin
                     ocur.per = oins + oexp;
                     osavep = ocur.cump / ocur.per;
                     ocur.iovere = (oins << 6) / oexp;
                  end
               end
            oflag = oinspir;
            if (omarker < 3)
               begin
                  if (oinspir) then
                     ++oins;
                  else
                     ++oexp;
               end
         end
      else omarker = 3;        /* if no O2 analyser connected, defeat loop */
   if (!(alm_counter || learn_count))   /* while not learning or alarming  */
      begin                             /* indicate inspiration or         */
         message = "_";                 /* expiration to show all OK       */
         if (p>= (average))
            message = "^";
         billb();
      end
end
if ( !relearn )
```

```
    begin
        cur.cump = savep;         /* retreive cump values from temporary storage */
        ocur.cump = osavep;
        if ((alm_priority < 37) && (!(learn_count == LRN_NUM)))
            if ( cur.iovere > MAX_IOE )           /* check I/E ratio against */
            begin                                 /* absolute limits         */
                message = "I/E > 4";
                alarm(37);
                alm_counter = 50;
            end
            else
            if ( cur.iovere < MIN_IOE )
            begin
                message = "I/E < .2";
                alarm(37);
                alm_counter = 50;
            end
    end
end /***************
*   COMPAR.DPM   *
***************
*
*   The routine compare() will compare the maximum pressure, the
*       minimum pressure, the period, the I/E ratio and the average
*       pressure of two breathing cycles. If a lack of agreement does
*       occur then error_type will be set to 1 and condition will
*       contain the priority of the disagreement.
*
*   THIS ROUTINE CALLS: normalize()
*
*   GLOBALS:
*       condition    = US = priority of a disagreement between the
*                             two cycles.
*       error_type   = US = 0 if two similar consequtive cycles have
*                             been found.
*       greater      = US = 1 if a < symbol in a message should be
*                             changed to a > symbol by the billb()
*                             routine.
*       omonitor     = US = set if an O2 analyser is connected
*       alm_priority = US = the priority of the currently active
*                             alarm condition.
*       ref          = ST = structure containing information about
*                             the reference cycle.
*       cur          = ST = structure containing information about
*                             the current cycle.
*       oref         = ST = structure containing information about
*                             the reference O2 cycle.
*       ocur         = ST = structure containing information about
*                             the current O2  cycle.
*       message      = PT = pointer to the current message.
*
*   STATIC LOCALS: none used
*
*   AUTOMATIC LOCALS: none used
*
*   ARGUMENTS:
*       comp_percent = US = a number which is 100 / ( the maximum
*                             allowed percent difference between the
*                             two cycles.
*
*   CONSTANTS: none used
*
***********************************************************************/ compare(comp_percent)
unsigned short comp_percent;
begin
    condition = 0;
    error_type = 1;
```

```
      greater = 0;
      if ( alm_priority < 60 )                         /* if there are no absolute alarms */
begin if (omonitor &&((normalize(olevel, osavelevel) < 20)))
   begin                                              /* if O2 concetration has changed */
      omonitor = 0;                                   /* during last cycle, disable O2   */
      condition = 59;                                 /* alarms.                          */
      message = "CHECK O2 SENSOR";
   end
if ( normalize( ref.maxp, cur.maxp) < (comp_percent+2) )
begin
      condition = 60;                                 /* check maximum pressure */
      message = "MAX PRESSURE < REFERENCE";
      if ( cur.maxp > ref.maxp )
         greater = 1;
end
else
if ( normalize( ref.minp, cur.minp) < comp_percent )
begin
      condition = 55;                                 /* check minimum pressure */
      message = "MIN PRESSURE < REFERENCE";
      if ( cur.minp > ref.minp )
         greater = 1;
end
else
if (normalize(ref.per,cur.per) < comp_percent)
begin
      condition = 50;                                 /* check period */
      message = "PERIOD < REFERENCE";
      if ( cur.per > ref.per )
         greater = 1;
end
else
if ( normalize(ref.cump,cur.cump) < comp_percent )
begin
      condition = 40;                                 /* check average pressure */
      message = "AVERAGE PRESSURE < REFERENCE";
      if ( cur.cump > ref.cump )
         greater = 1;
end
else
if ( normalize(ref.iovere,cur.iovere) < (comp_percent-2) )
begin
      condition = 35;                                 /* check I/E ratio */
      message = "I/E < REFERENCE";
      if ( cur.iovere > ref.iovere )
         greater = 1;
end
else
if (( normalize( oref.maxp, ocur.maxp) < (comp_percent+2) ) && (omonitor))
begin
      condition = 57;                                 /* check O2 maximum pressure */
      message = "CHECK O2 SENSOR";
end
else
if (( normalize( oref.minp, ocur.minp) < comp_percent ) && (omonitor))
begin condition = 53;                                 /* check O2 minimum pressure */
      message = "CHECK O2 SENSOR";
end
else
if ((normalize( oref.per, ocur.per) < comp_percent)  && (omonitor))
begin
      condition = 47;                                 /* check O2 period */
      message = "CHECK O2 SENSOR";
end
else
if (( normalize(oref.cump,ocur.cump) < comp_percent ) && (omonitor))
begin
```

```
            condition = 37;                              /* check O2 average pressure */
            message = "CHECK O2 SENSOR";
        end
        else
        if (( normalize(oref.iovere,ocur.iovere) < (comp_percent-2)) && (omonitor))
        begin
            condition = 33;                              /* check O2 I/E ratio */
            message = "CHECK O2 SENSOR";
        end
        else   error_type = 0;                           /* no errors detected */
    end
end /***************
*  BILLB.DPM  *
***************
*
*  The routine billb() will copy the character string in message
*       into the character array rev_message so that 8 blanks will
*       precede the first character from message and an additional
*       8 blanks will follow the last character. If 'window' is not
*       equal to 0 then the first 8 characters of rev_message will
*       be displayed otherwise 8 characters starting at the 9th
*       character will be displayed.
*
*       THIS ROUTINE CALLS:   displ()
*                             out()
*
*       GLOBALS:   window = UC = 0 if message displayed without
*                                   billboarding.
*                               = 1 if message displayed with
*                                   billboarding.
*                  message = UC = character string which contains the
*                                   string to be displayed.
*                  r_mes   = PT = pointer to rev_message string
*                  length  = US = length of current message
*                  greater = US = flag which indicates whether a < in the
*                                   message should be converted into a >
*
*       STATIC LOCALS:   none used
*
*       AUTOMATIC LOCALS:
*                   step = US = loop counter and index for rev_message.
*
*       ARGUMENTS:   none used
*
*       CONSTANTS:
*                   DISPLAY = output port for leftmost character
*                                in display.
*
**********************************************************************/
billb()
begin
    unsigned short step;
    for (step=0; step<=7; step++)   /* set first 8 characters of message blank*/
        rmes[step]=' ';
    length=8;
    for (step=0; message[step] != '\0'; step++)   /* while not end of message,*/
    begin                                         /* copy to rmes buffer and  */
                                                  /* set > or < as appropriate*/
        rmes[step+8] = ((message[step]=='<')&&greater) ? '>':message[step];
        length++;           /* Keep track of length of message to be displayed */
    end
    greater = 0;
    for (step=(length); step <= 7+length; step++)  /* fill end of message with*/
        rmes[step]=' ';                            /* 8 blanks.              */
    window = (length > 16) ? 1 : 0;  /* if message > 8 characters, set window */
    for (step=0; step <= 7; step++)                          /* display message */
        out(DISPLAY-step,rmes[(window ? 0 : 8)+step]);
end
```

```
/***************
 *  ALARM.DPM  *
 ***************
 *
 *   The routine alarm() checks if the current alarm condition has a
 *       higher alarm priority than the presently active alarm.  If
 *       so, the current alarm message is billboarded.
 *
 *       THIS ROUTINE CALLS: billb()
 *
 *       GLOBALS:
 *           alm_priority = US = priority of the presently active alarm
 *           alm_counter  = US = number of interrupts left for the
 *                               presently active alarm.
 *           error_type   = US = flag indicating type of relative error
 *
 *       ARGUMENTS:
 *           prio         = US = priority of the current alarm condition
 *
 *
 *       CONSTANTS: none used
 *
 ******************************************************************/ alarm(prio)
    unsigned short prio;
begin
    error_type = 2;                     /* set flag indicating error condition */
    if ( prio > alm_priority )          /* if latest alarm has higher priority */
    begin
        alm_priority = prio;
        billb();                                        /* display new alarm */
        alm_counter = (length << 2) - 1;   /* leave alarm on long enough to */
    end                                                 /* display message twice.    */
end /**********
 * CAL.DPM *
 **********
 *   The routine caltest() displays the present value of pressure, battery
 *       voltage, or external signals 1 and 2 on the alphanumeric display.
 *
 *       THIS ROUTINE CALLS:
 *           billb()
 *           caltest()
 *
 *       GLOBALS:
 *           message   = UC = pointer to current message string
 *           relearn   = US = flag indicating if relearn has been pressed
 *           status    = US = flag set to indicate that a trap has occurred
 *           calibrate = US = flag set to indicate calibrate mode selected
 *           olevel    = US = latest O2 concentration
 *           opress    = US = latest O2 pressure reading
 *              p      = US = latest pressure reading
 *              bat    = US = latest battery voltage reading
 *
 *       AUTOMATIC LOCALS: none used
 *
 *       ARGUMENTS: none used
 *
 *       CONSTANTS: none used
 *
 ******************************************************************/
caltest()
begin
    calibrate = 0;                      /* as long as calibrate mode is not */
    learnflag = 0;                      /* a second time, loop through sub- */
    while (!calibrate)                  /* modes.                           */
      begin
        while ((!relearn) && (!calibrate))
```

```
          begin                                  /* until relearn switch is hit, */
            status = 0;                          /* display current pressure.    */
            while (!status)
              ;
            message = "   P=    ";
            billb();
            translate(p);              /* convert number to ASCII and display */
          end
        status = 0;
        while (!status)
          ;
        while ((!relearn) && (!calibrate))
          begin                                  /* until relearn switch is hit, */
            status = 0;                          /* display current battery volts*/
            while (!status)
              ;
            message = " BAT=    ";
            billb();
            translate(bat);            /* convert number to ASCII and display*/
          end
        status = 0;
        while (!status)
          ;
        while ((!relearn) && (!calibrate))
          begin                                  /* until relearn switch is hit, */
            status = 0;                          /* display current AUX1 level.  */
            while (!status)
              ;
            message = "AUX1=    ";
            billb();
            translate(olevel);         /* convert number to ASCII and display*/
          end
        status = 0;
        while (!status)
          ;
        while ((!relearn) && (!calibrate))
          begin                                  /* until relearn switch is hit, */
            status = 0;                          /* display current AUX2 level.  */
            while (!status)
              ;
            message = "AUX2=    ";
            billb();
            translate(opress);         /* convert number to ASCII and display*/
          end
        status = 0;
        while (!status)
          ;
      end
calibrate = 0;          /* ensure that calibrate is not immediatly re-entered */
learnflag = 0;
end /************
* TRANS.DPM *
*************
*
*       The routine translate() changes the unsigned short value into
*       ASCII characters representing its hex value, and inserts them
*       into the 6th and 7th message positions. This routine is used
*       by the routine caltest() so that the values being returned
*       by the analog to digital converter can be displayed on the
*       alphnumeric displays.
*
*       THIS ROUTINE CALLS: nothing
*
*       GLOBALS:
*               message = UC = pointer to current message
*
*       STATIC LOCALS: none
*
```

```
*           AUTOMATIC LOCALS:
*                   temp = US = temporary register for argument
*
*           ARGUMENTS:
*                   value = US = value to be converted to ascii
*
*           CONSTANTS:
*                   DISPLAY = first display location port address
*
************************************************************************/ translate(value)
unsigned short value;
begin
   unsigned short temp=0;
   temp = (((value & 0x00F0) >> 4) + 48);   /* mask off lower 4 bits and con- */
   if (temp > 57) temp = temp + 7;          /* vert to ASCII code for hex     */
   out (DISPLAY - 6, temp);                 /* value and display in LSB.      */
   temp =((value & 0x000F) + 48);           /* mask off upper 4 bits and con- */
   if (temp > 57) temp = temp + 7;          /* vert to ASCII code for hex     */
   out (DISPLAY - 7, temp);                 /* value and display in LSB+1     */
end /***************
*   SENSE.DPM   *
****************
*
*   The routine sense() will wait for an interrupt, determine if the
*       current pressure is an extreme for the present cycle and then
*       add the pressure to the cumulative total for the present cycle.
*       If the pressure is sufficiently high, the low pressure counter
*       is reset to NOPRESTIME.
*
*       GLOBALS:
*               p           = US = current pressure conversion
*               opress      = US = current O2 pressure conversion
*               ocur        = ST = structure which contains information about
*                                  the currrent O2 cycle
*               oref        = ST = structure which contains information about
*                                  the reference O2 cycle
*               cur         = ST = structure which contains information about
*                                  the current cycle.
*               ref         = ST = structure containing information about the
*                                  reference cycle.
*           rout_count      = US = counter which is decremented on each
*                                  interrupt.
*
*       STATIC LOCALS: none used
*
*       AUTOMATIC LOCALS: none used
*
*       ARGUMENTS: none used
*
*       CONSTANTS:
*               AVG_HYS     = hysteresis used in checking for transition from
*                             expiratory to inspiratory or vice versa.
*           NO_PRES_DIFF    = minimum pressure change from minimum pressure
*                             of reference cycle.
*               NOPRESTIME  = number of interrupts allowed before low pressure
*                             alarm condition appears.
*
************************************************************************/
sense()
begin
    status = 0;
    while ( !status )                               /* wait for an interrupt */
        ;
    if ( p > cur.maxp )  cur.maxp = p;      /* detects highest pressure reading */
    if ( p < cur.minp )  cur.minp = p;      /* detects lowest pressure reading */
```

```
   cur.cump += p;                                                   /* cumulative pressure */
   if ( opress > ocur.maxp )   ocur.maxp = opress;                  /* high and low O2     */
   if ( opress < ocur.minp )   ocur.minp = opress;                  /* pressure readings*/
   ocur.cump += opress;                                              /* cumulative O2 pressure */
                            /* if pressure is varying, keep seting rout_count */
   if ((p >= (ref.cump + AVG_HYS)) && (p >= (ref.minp+NO_PRES_DIFF)))
       rout_count = NOPRESTIME;
end /***************
*   NORM.DPM    *
****************
*
*   The routine normalize() will return a number which is 100 / ( the
*       percent difference between two numbers ) since this number
*       is equal to the reference number divided the difference between
*       the two numbers. If the two numbers are the same then 100 is
*       returned.
*
*       THIS ROUTINE CALLS:
*
*       GLOBALS:
*           percent = US = 100 / ( the percent difference between the values)
*
*       STATIC LOCALS: none used
*
*       AUTOMATIC LOCALS:
*           diff    = US = the difference between the two numbers.
*
*       ARGUMENTS:
*           val1    = US = the reference number of the two numbers to
*                           be compared.
*           val2    = US = the second of the two numbers.
*
*       CONSTANTS: none used
*
*******************************************************************************/ normalize(val1,val2)
unsigned short val1;
unsigned short val2;
begin
unsigned short diff;
    if ( val2 > val1 )      /* find the larger value and calculate difference */
        diff = val2 - val1;
    else
        diff = val1 - val2;
    if (diff == 0) percent = 100;           /* if values are equal set to 100 */
    else    percent = val1 / diff;          /* calculate the inverse percentage */
    return(percent);
end /***************
*   ADCMN.DPM   *
****************
*
*   The routine adcmn() starts the A/D conversion of either the
*       the pressure or the battery voltage. When an end of conversion
*       signal appears the digital representation is input from the
*       A/D and returned to the calling routine.
*
*       THIS ROUTINE CALLS: out()
*                           in()
*
*       GLOBALS: none used
*
*       STATIC LOCALS: none used
*
*       AUTOMATIC LOCALS:  none used
```

```
*
*           ARGUMENTS:
*               adcpt = US = port number to start A/D conversion of
*                               appriopriate signal.
*
*           CONSTANTS:
*               PB = port number of register correspponding to port B on 810
*
*********************************************************************/
adcmn(adcpt)
unsigned short adcpt;
begin
    out(adcpt,0);                              /* start conversion */
    while ((in(PB) & 0x01) == 0)               /* wait for end of conversion */
    ;
    return(in(adcpt));                         /* return */
end
```

I claim:

1. A method for detecting an interruption in the supply of breathing gas to a patient, comprising the steps of:
   during a predetermined time period within at least one breathing cycle of a patient initiated solely by an operator and significant of a reference time period during which a normal breathing cycle of the patient occurs, sensing the pressure in the patient's breathing gas;
   deriving from the pressure sensed during the reference time period, reference breathing information including a reference breathing cycle waveform parameter,
   storing, in memory apparatus, the reference breathing information including said reference breathing cycle waveform parameter derived from the pressure sensed during said reference time period;
   after said reference time period, sensing the pressure in the patient's breathing gas and deriving from the pressure sensed after said reference time period, active breathing information including an active breathing cycle waveform parameter;
   comparing the active breathing information including said active breathing cycle waveform parameter derived from the pressure sensed after said reference time period with said reference breathing information including said reference breathing cycle waveform parameter; and,
   producing an alarm signal upon detection, during said comparing step, of a predetermined variation between the breathing cycle waveform parameters of said reference breathing information and said active breathing information, respectively.

2. A method as defined in claim 1, further comprising:
   before said storing step, referentially comparing:
   the reference breathing information derived from the pressure in the patient's breathing gas during a first referential breathing cycle of the patient; and,
   second reference breathing information derived from the pressure in the patient's breathing gas during a second referential breathing cycle of the patient which follows said first referential breathing cycle;
   proceeding to said storing step if said breathing information derived from said pressure sensed during said first referential breathing cycle differs, by no more than a selected amount, from said breathing information derived from said pressure sensed during said second referential breathing cycle; and,
   repeating said referential comparing step if said reference breathing information derived from said pressure sensed during said first referential breathing cycle differs, by more than a selected amount, from said second reference breathing information derived from said pressure sensed during said second referential breathing cycle.

3. A method as defined in claim 2, further comprising producing said alarm signal upon detection, during said reference time period, of ten successive referential breathing cycles, each having an average pressure which differs, by more than about ten percent, from the average pressure of the immediately following referential breathing cycle.

4. A method as defined in claim 1, wherein said breathing information includes the average. breathing gas pressure sensed during the breathing cycle in respect of which said breathing information is derived.

5. A method as defined in claim 4, further comprising producing said alarm signal upon detection, for at least 15 seconds during an active breathing cycle, of breathing gas pressures less than the greater of:
   (a) 5 cmH$_2$O; and,
   (b) the average breathing gas pressure of said representative normal breathing cycle.

6. A method as defined in claim 1, wherein said breathing information includes the maximum breathing gas pressure sensed during the breathing cycle in respect of which said breathing information is derived.

7. A method as defined in claim 1, wherein said breathing information includes the minimum breathing gas pressure sensed during the breathing cycle in respect of which said breathing information is derived.

8. A method as defined in claim 1, wherein said breathing information includes the ratio of the time, during the breathing cycle in respect of which said breathing information is derived, the patient inspires breathing gas, to the time, during the breathing cycle in respect of which said breathing information is derived, the patient expires breathing gas.

9. A method as defined in claim 1, wherein said breathing information includes the period of the breathing cycle in respect of which said breathing information is derived.

10. A method as defined in claim 1, further comprising producing said alarm signal upon detection of an active breathing cycle having a period longer than about 30 seconds.

11. Apparatus for detecting an interruption in the supply of breathing gas to a patient, said apparatus comprising:

pressure sensing means for sensing the pressure in the patient's breathing gas during a breathing cycle of a patient and for producing an output signal representative thereof;

means for deriving breathing information including a reference breathing cycle waveform parameter from said output signal during a predetermined time period within at least one of said breathing cycles significant of a reference time period during which a normal breathing cycle of a patient occurs;

memory means for storing said reference breathing information including said reference breathing cycle waveform parameter derived from said output signal during said reference time period;

means solely actuable by an operator for initiating the reference time period to cause storage of said reference breathing information including said reference breathing cycle waveform parameter;

means for deriving active breathing information including an active breathing cycle waveform parameter from said output signal after said reference time period;

signal comparison means for comparing:
active breathing information including said active breathing cycle waveform parameter derived from said output signal after said reference time period; with
said reference breathing information including said reference breathing cycle waveform parameter derived from said output signal; and, alarm means for producing an alarm signal upon detection, by said comparison means, of a predetermined variation between said breathing cycle waveform parameters of said active breathing information and said reference breathing information.

12. Apparatus as defined in claim 11, wherein said pressure sensing means is an electronic pressure transducer.

13. Apparatus as defined in claim 11, wherein said alarm means comprises an audible alarm for producing an audible alarm signal.

14. Apparatus as defined in claim 13, further comprising alarm suppression means for suppressing said audible alarm signal.

15. Apparatus as defined in claim 14, wherein said alarm suppression means suppresses said audible alarm signal for no more than about 30 seconds.

16. Apparatus as defined in claim 11 or 13, wherein said alarm means further comprises display means for displaying a visible message representative of said predetermined variation, upon detection thereof.

17. Apparatus as defined in claim 11, further comprising status indicator means for indicating an absence of detection, by said comparison means, of said predetermined variation.

18. Apparatus as defined in claim 11, further comprising control means for enabling replacement of said reference breathing information with revised reference breathing information derived from said output signal.

19. Apparatus as defined in claim 18, wherein storage of reference breathing information is prevented while said alarm signal is produced.

* * * * *

UNITED STATES PATENT AND TRADEMARK OFFICE
CERTIFICATE OF CORRECTION

PATENT NO. : 4,550,726
DATED : November 5, 1985
INVENTOR(S) : JAMES A. MCEWEN

It is certified that error appears in the above-identified patent and that said Letters Patent is hereby corrected as shown below:

Column 2, line 47 after "pressure" insert --variations during successive cycles of inhalation--;

Column 2, line 59, "breting" should be --breathing--;

Column 3, line 18, "indiated" should be --initiated--;

Column 4, line 60, "operation" should be --operator--;

Column 5, line 9, "interuption" should be --interruption--;

Column 6, lines 10, 11, delete "patient breathing circuit and has returned to its normal";

Column 6, line 16, "mobitor" should be --monitor--;

Column 6, line 61, "27-30" should be --2-30--;

UNITED STATES PATENT AND TRADEMARK OFFICE
CERTIFICATE OF CORRECTION

PATENT NO. : 4,550,726

DATED : November 5, 1985

INVENTOR(S) : JAMES A. MCEWEN

It is certified that error appears in the above-identified patent and that said Letters Patent is hereby corrected as shown below:

Column 10, line 52, "dicussion" should be --discussion--;

Column 12, line 30, "suffieiently" should be --sufficiently--;

Column 19, line 68, "condition" should be --conditions--;

Column 20, line 34, "valves" should be --values--.

Signed and Sealed this

Tenth Day of June 1986

[SEAL]

Attest:

DONALD J. QUIGG

Attesting Officer

Commissioner of Patents and Trademarks